(12) United States Patent
Kim et al.

(10) Patent No.: US 10,085,704 B2
(45) Date of Patent: Oct. 2, 2018

(54) X-RAY IMAGING APPARATUS AND CONTROL METHOD FOR THE SAME

(71) Applicant: SAMSUNG ELECTRONICS CO., LTD., Suwon-si (KR)

(72) Inventors: Sung Su Kim, Yongin-si (KR); Hyun Hwa Oh, Hwaseong-si (KR); Dong Goo Kang, Hwaseong-si (KR); Sung Hoon Kang, Suwon-si (KR); Young Hun Sung, Hwaseong-si (KR); Kang Eui Lee, Seoul (KR); Seok Min Han, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 1171 days.

(21) Appl. No.: 14/282,623

(22) Filed: May 20, 2014

(65) Prior Publication Data

US 2014/0341336 A1    Nov. 20, 2014

(30) Foreign Application Priority Data

May 20, 2013  (KR) ........................ 10-2013-0056517

(51) Int. Cl.
*A61B 6/00* (2006.01)
(52) U.S. Cl.
CPC ............ *A61B 6/502* (2013.01); *A61B 6/4488* (2013.01)

(58) Field of Classification Search
CPC .............................. A61B 6/4488; A61B 6/502
See application file for complete search history.

(56) References Cited

U.S. PATENT DOCUMENTS

| 2004/0206738 | A1 | 10/2004 | Argersinger et al. |
| 2008/0247508 | A1 | 10/2008 | Harrington et al. |
| 2010/0243894 | A1* | 9/2010 | Kato ........................ G01T 7/00 250/336.1 |

FOREIGN PATENT DOCUMENTS

| JP | 2005-349207 A | 12/2005 |
| JP | 2010-35622 A | 2/2010 |
| JP | 2012-108110 A | 6/2012 |

* cited by examiner

*Primary Examiner* — Dani Fox
(74) *Attorney, Agent, or Firm* — Sughrue Mion, PLLC

(57) ABSTRACT

An X-ray imaging apparatus and method for controlling the X-ray imaging apparatus are provided. The X-ray imaging apparatus includes an X-ray source configured to generate and emit X-rays onto an object, an X-ray detector configured to detect the X-rays transmitted through the object and convert the X-rays into an electrical signal, a heating portion located at an upper portion of the X-ray detector configured to contact a lower part of the object, a heat transfer portion configured to transfer heat produced in the X-ray source to the heating portion, and a thermal insulation member located between the X-ray detector and the heating portion configured to block heat from being transferred to the X-ray detector.

20 Claims, 22 Drawing Sheets

X-RAY IMAGING APPARATUS AND CONTROL METHOD FOR THE SAME

CROSS-REFERENCE TO RELATED APPLICATION

This application claims priority from Korean Patent Application No. 2013-0056517, filed on May 20, 2013 in the Korean Intellectual Property Office, the disclosure of which is incorporated herein by reference in its entirety.

BACKGROUND

1. Field

Apparatuses and methods consistent with the exemplary embodiments relate to an X-ray imaging apparatus which produces an X-ray image by transmitting X-rays through an object, such as a human breast, and a control method for the same.

2. Description of the Related Art

An X-ray imaging apparatus is designed to emit X-rays onto an object and acquire an image of the internal structure of the object using the X-rays which are transmitted through the object. Since the transmission of the X-rays depends on the properties of the materials constituting the object, an image of the inner structure of the object may be obtained by detecting the intensity or strength of the X-rays transmitted through the object.

An X-ray imaging apparatus for imaging, for example, a human breast is structurally different from other X-ray imaging apparatuses for imaging other kinds of tissues. Since the breast includes large amounts of glandular tissue and fatty tissue, X-ray imaging needs to be performed while the breast is positioned between an X-ray source and an X-ray detector is compressed by a compression paddle, in order to obtain a sharp X-ray image which clearly shows the internal structure of the breast. To this end, the breast is positioned on the upper portion of the X-ray imaging apparatus and compressed with a compression paddle.

The scanning room where the X-ray imaging apparatus is installed may be maintained at a temperature which may be too cold for a patient. Therefore, a patient having their breast imaged will feel discomfort from the compression of the compression paddle. Further, the patent may feel discomfort and cold since they have to remove their clothing from the waist up.

SUMMARY

Therefore, it is an aspect of an exemplary embodiment to provide an X-ray imaging apparatus and a control method for the same which uses heat which is dissipated during the generation of X-rays to heat the portion of the X-ray imaging apparatus which contacts the breast during X-ray imaging of the breast. Therefore, discomfort which the subject may feel due to the cold may be reduced and a separate heat source is not required.

Additional aspects of the exemplary embodiments will be set forth in part in the description which follows and, in part, will be obvious from the description, or may be learned by practice of the exemplary embodiments.

In accordance with one aspect of an exemplary embodiment, an X-ray imaging apparatus which captures an X-ray image of an object includes an X-ray source configured to generate and emit X-rays onto an object, an X-ray detector configured to detect the X-rays transmitted through the object and convert the detected X-rays into an electrical signal, a heating portion located at an upper portion of the X-ray detector configured to contact a lower part of the object, a heat transfer portion configured to transfer heat produced in the X-ray source to the heating portion, and a thermal insulation member located between the X-ray detector and the heating portion configured to block heat from being transferred to the X-ray detector.

The heat transfer portion may include a pipe through which a fluid heated by the heat produced in the X-ray source flows.

The X-ray imaging apparatus may further include a flow regulator configured to regulate a flow of the fluid.

The heating portion may include a passage through which the fluid circulates, and wherein the passage includes at least one curved portion.

The X-ray imaging apparatus may further include a heat storage portion configured to store the heat produced in the X-ray source.

The X-ray imaging apparatus may further include a temperature sensor configured to measure a temperature of the heating portion.

The X-ray imaging apparatus may further include a temperature controller configured to control the flow regulator based on the temperature of the heating portion measured by the temperature sensor.

In accordance with another aspect of an exemplary embodiment, a control method for an X-ray imaging apparatus which captures an X-ray image of an object includes supplying electric power to an X-ray tube and producing X-rays and heat, storing the produced heat in a heat storage portion, and transferring the stored heat to a heating portion to contact an object.

BRIEF DESCRIPTION OF THE DRAWINGS

These and/or other aspects of the exemplary embodiments will become apparent and more readily appreciated from the following description of the exemplary embodiments, taken in conjunction with the accompanying drawings of which.

DETAILED DESCRIPTION

Figure 1:
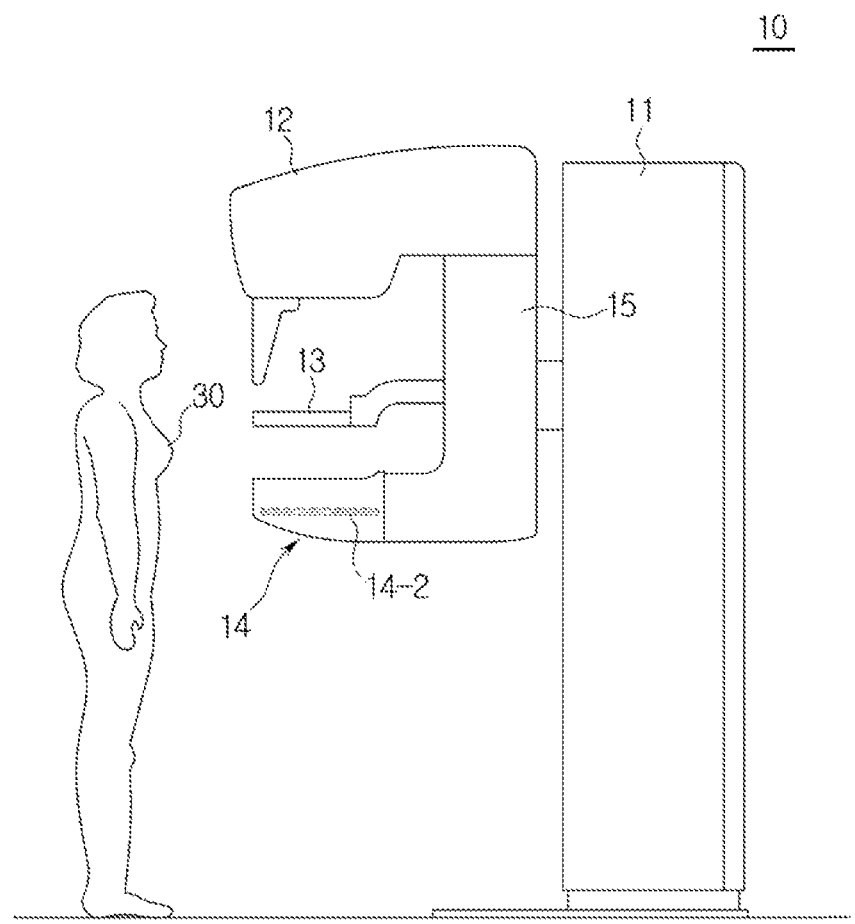
FIG. 1 is a view showing an external appearance of an X-ray imaging apparatus for X-ray imaging of the breast.

Reference will now be made in detail to the exemplary embodiments, examples of which are illustrated in the accompanying drawings, wherein like reference numerals refer to like elements throughout.

FIG. 1 is a view showing an external appearance of an X-ray imaging apparatus used for performing X-ray imaging of a breast.

The X-ray imaging apparatus 10 used for performing X-ray imaging of the breast is specifically designed for mammography, unlike a typical X-ray imaging apparatus. Specifically, as shown in FIG. 1, an X-ray source 12 and an X-ray detector assembly 14 are mounted on a body 11. When the X-ray source 12 emits X-rays onto a breast 30 positioned between the X-ray source 12 and the X-ray detector assembly 14, an X-ray detector 14-2 detects the X-rays transmitted through the breast 30 to acquire an X-ray image of the breast 30.

The X-ray imaging apparatus 10 further includes a compression paddle 13 installed between the X-ray source 12 and the X-ray detector assembly 14. The compression paddle 13 compresses an object, such as the breast 30, which is placed on the X-ray detector assembly 14. Hereinafter, operation of the compression paddle 13 will be described in detail with reference to FIGS. 2 and 3.

Figure 2:
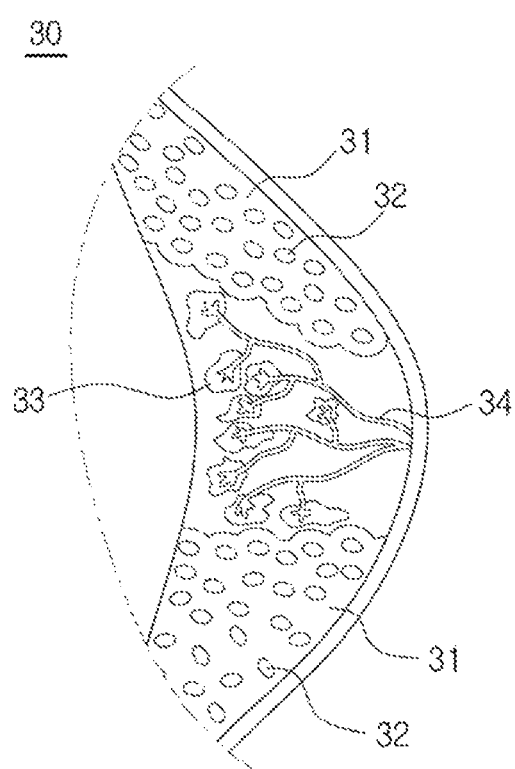
FIG. 2 a cross-sectional view illustrating an internal structure of a breast.
Figure 3:
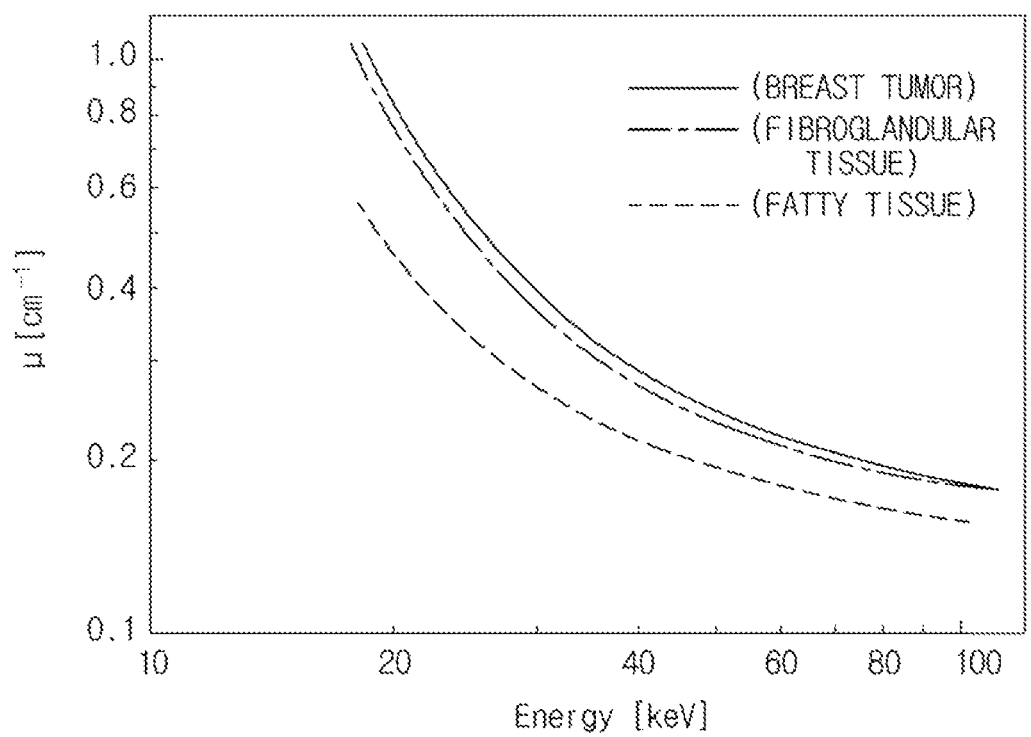
FIG. 3 is a graph showing X-ray attenuation coefficients of parts constituting the breast including breast tumors, fibroglandular tissue and fatty tissue in respective energy bands.

FIG. 2 a cross-sectional view illustrating an internal structure of a breast, and FIG. 3 is a graph showing X-ray attenuation coefficients of the parts constituting the breast.

Referring to FIG. 2, the tissues of the breast 30 include fibrous tissue 31 which surrounds the breast to maintain the form of the breast, fatty tissue 32 which is distributed through the breast, glandular tissue 33 to produce breast milk, and connective tissue 34 which functions as ducts for movement of breast milk. Glandular tissue 33 and connective tissue 34, which are related to production and supply of breast milk, are referred to as fibroglandular tissue.

The attenuation coefficients are data which indicate the degrees to which the transmitted X-rays are attenuated. Since each material constituting the internal structure of an object has a different attenuation coefficient, an image of the internal structure of the object may be obtained by transmitting X-rays to the object.

FIG. 3 is a graph showing X-ray attenuation coefficients of parts in a breast including a breast tumor, fibroglandular tissue and fatty tissue in the respective energy bands. As shown in FIG. 3, the difference in attenuation coefficient among materials constituting the breast is not large. This is because the breast is composed of soft tissue alone, as shown in FIG. 2. Therefore, to acquire as sharp an X-ray image as possible, the breast is compressed with the compression paddle 13 to decrease the thickness of the breast. As the thickness of the breast decreases, an X-ray exposure dose may also be reduced.

Referring to FIG. 1, the compression paddle 13 may be mounted to a frame 15 connecting the X-ray source 12 with the X-ray detector assembly 14 to vertically move. Once the breast 30 is placed on the X-ray detector assembly 14 to perform X-ray imaging, the compression paddle 13 compresses the breast 30, and X-ray imaging of the breast 30 is performed through emission and detection of X-rays, with the breast 30 compressed.

Among the components of the X-ray imaging apparatus 10, there are temperature sensitive devices. Particularly, since the X-ray detector 14-2 includes semiconductor devices, the X-ray imaging apparatus 10 may fail to operate normally and may cause errors unless the temperature is maintained at a level suitable for the properties of the temperature sensitive devices. Therefore, the scanning room, for example, a room in a clinic or hospital where the X-ray imaging apparatus 10 is installed, and the X-ray imaging apparatus 10 are maintained at a certain temperature suitable for the properties of the temperature sensitive devices.

However, the temperature suitable for the properties of the temperature sensitive devices is relatively low and therefore, a human in the scanning room especially a human whose breast is being imaged, may feel cold. Specifically, a subject, such as a human patient whose breast is being imaged, may have to remove their clothing from the waist up, and will therefore feel cold while in the scanning room Moreover, since the part of the X-ray imaging apparatus 10 which contacts and compresses the breast is cold, discomfort may be caused by pain from compression and cold.

The X-ray imaging apparatus according to the illustrated exemplary embodiment minimizes patient discomfort by raising the temperature of the part of the X-ray imaging apparatus 10 which contacts the breast. Hereinafter, the configuration and operation of the X-ray imaging apparatus according to one exemplary embodiment will be described FIG. 4 is a side view showing an external appearance of an X-ray imaging apparatus according to an exemplary embodiment, FIG. 5A is a view schematically illustrating a configuration of an X-ray tube according to the exemplary embodiment, and FIG. 5B is a view schematically illustrating a configuration of an X-ray detector according to the exemplary embodiment.

Figure 4:
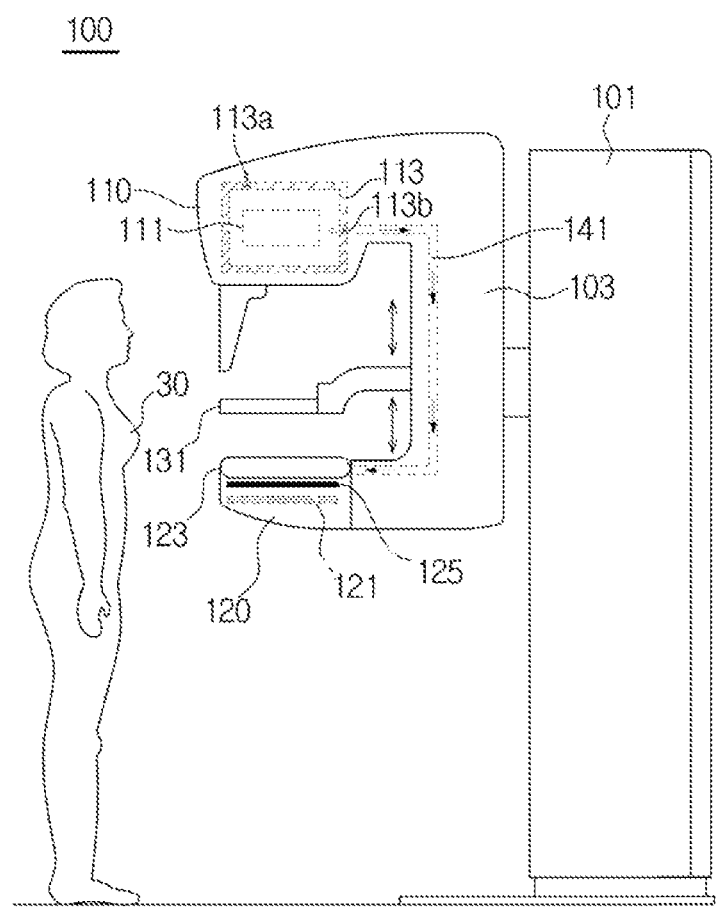
FIG. 4 is a side view showing an external appearance of an X-ray imaging apparatus according to an exemplary embodiment.
Figure 5A:
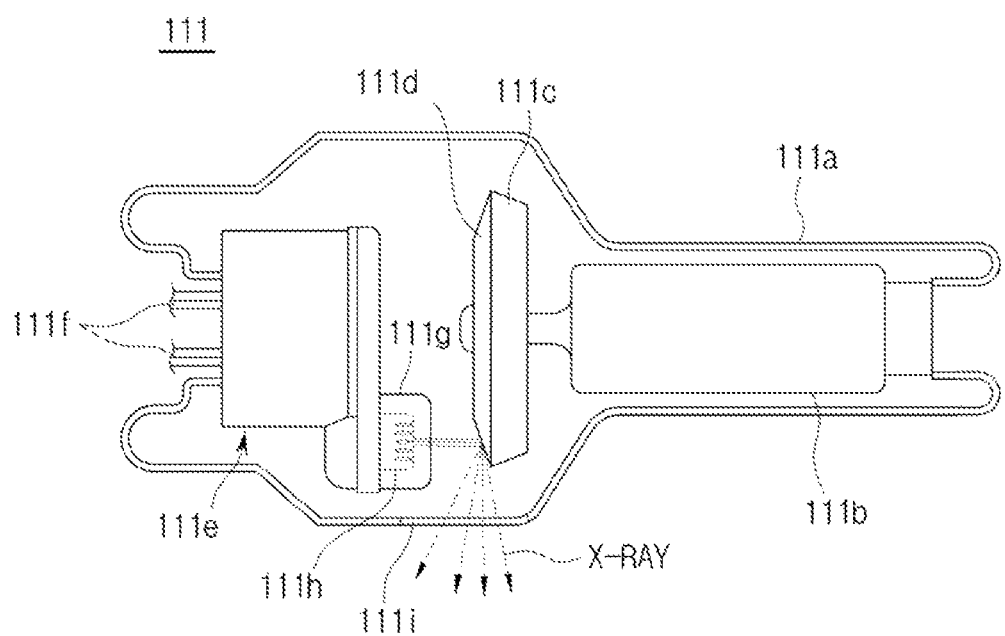
FIG. 5A is a view schematically illustrating a configuration of an X-ray tube according to the exemplary embodiment.
Figure 5B:
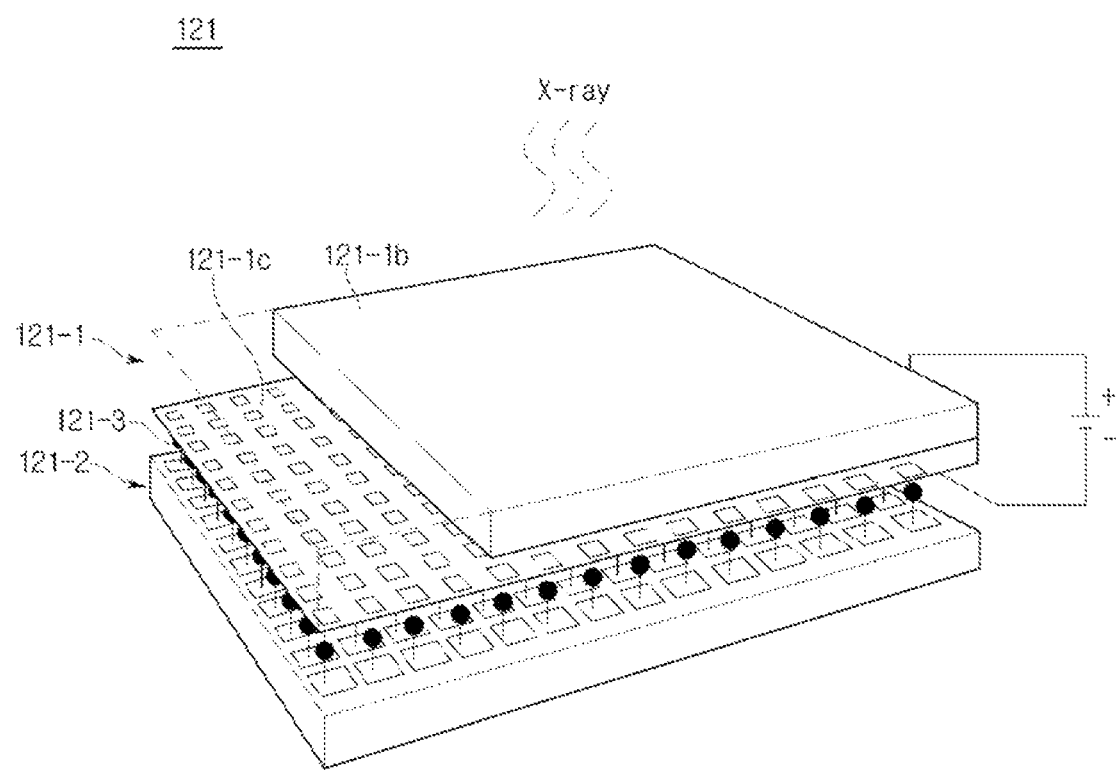
FIG. 5B is a view schematically illustrating a configuration of an X-ray detector according to the exemplary embodiment.

Referring to FIG. 4, the X-ray imaging apparatus 100 includes an X-ray source 110 to generate X-rays and emit the X-rays onto the breast 30, an X-ray detector assembly 120 to detect the X-rays transmitted through the breast 30, and a compression paddle 131 to compress the object, such as the breast 30, positioned on the X-ray detector assembly 120. The X-ray source 110 is connected with the X-ray detector assembly 120 by a frame 103, and the frame 103 is mounted to a body 101.

The X-ray source 110 includes an X-ray tube 111 which generates an X-ray. This tube is referred to as an X-ray tube head or an X-ray tube assembly. Referring to FIG. 2A, the X-ray tube 111 may be realized as a tube 111a containing two electrodes including an anode electrode 111c and a cathode electrode 111e, and the body of the X-ray tube 111 may be a glass tube formed of hard silica glass.

The cathode 111e includes a filament 111h and a focusing electrode 111g to focus electrons. The focusing electrode 111g is also referred to as a focusing cup. By creating a high vacuum of about 10 mmHg in the glass tube 111a and heating the filament 111h of the cathode, thermal electrons are generated. A tungsten filament may be used as the filament 111h. The filament 111h may be heated by applying current to an electric wire 111f connected to the filament 111h.

The anode 111c is typically formed of copper. A target material 111d is applied to or located on the side of the anode 111c facing the cathode 111e. The target material can be a material which has a high resistance, such as chromium (Cr), iron (Fe), cobalt (Co), nickel (Ni), tungsten (W), and molybdenum (Mo). As the melting point of the target material increases, the size of the focal spot increases.

When a high voltage is applied between the cathode 111e and the anode 111c, thermal electrons are accelerated to collide with the target material 111d of the anode 111c to produce X-rays. The produced X-rays are emitted outside of the X-ray tube 111 through a window 111i. The window 111i may be made of a thin film of beryllium (Be). A filter (not shown) may be positioned at the front or rear surface of the window 111i to filter out X-rays in a specific energy band.

The target material 111d may be rotated by a rotor 111b. When the target material 111d is rotated, the heat storage capacity per unit area may be increased by more than about 10 times from the heat storage capacity per unit area of that obtained by fixing the target material 111d, and the size of the focal spot may be reduced.

The voltage applied between the cathode 111e and anode 111c of the X-ray tube 111 is referred to as tube voltage. The magnitude of the tube voltage may be represented as peak kilovoltage (kVp). An increase in the tube voltage leads to an increase in speed of thermal electrons, thereby resulting in an increase in X-ray energy (the photon energy) produced when thermal electrons strike the target material. The electric current flowing through the X-ray tube 111 is referred to as tube current and may be represented by average current (mA). An increase in the tube current leads to an increase in X-ray dose (the number of X-ray photons).

Accordingly, X-ray energy may be controlled by adjusting the tube voltage, and the intensity or dose of X-rays may be controlled by adjusting tube current and X-ray exposure time. Therefore, the energy and dose of X-rays to be emitted may be controlled according to the type and properties of the object, such as the breast 30.

In the case that the emitted X-rays are in a certain energy band, the energy band may be defined by upper and lower limits. The upper limit of the energy band, i.e., the maximum energy of the emitted X-rays may be adjusted by adjusting the tube voltage, and the lower limit of the energy band, i.e., the minimum energy of the emitted X-rays may be adjusted by the filter. By filtering out X-rays in a low energy band using the filter, the average energy value of the emitted X-rays may be increased.

When thermal electrons strike the target material 111d, the efficiency of X-ray production is less than 1%. That is, less than 1% of the energy of the thermal electrons is converted into X-rays and the other portion of the energy is converted into heat. Therefore, when X-rays are produced, heat is produced at the anode 111c of the X-ray tube 111. The produced heat, which is waste heat, dissipates from the glass tube 111a. Accordingly, if the anode 111c is rotated as described above, the heat dissipation efficiency may be increased.

The X-ray imaging apparatus 100 may heat the part of the X-ray imaging apparatus 100 which contacts the object, such as the breast 30, without using a separate heat source by transferring the waste heat produced in the X-ray tube 111 to the X-ray detector assembly 120.

Referring to FIG. 4, the X-ray tube 111 is surrounded by a housing 113. The housing 113 is provided with a fluid inlet 113a through which the fluid flows into the housing 113, and a fluid outlet 113b through which the fluid is discharged from the housing 113. The fluid serves as a medium to absorb the heat dissipated from the X-ray tube 111 and transfers the absorbed heat to the X-ray detector assembly 120. That is, heat produced in the X-ray tube 111 may be transferred to a part of the X-ray imaging apparatus 100 which contacts the breast through a medium like the fluid. The fluid may be at least one selected from a group including air, cooling water or cooling oil. However, the type of the fluid is not limited so long as the fluid is capable of absorbing and dissipating heat.

The fluid introduced through the fluid inlet 113a absorbs heat dissipated from the X-ray tube 111. The fluid which has absorbed the heat is discharged through the fluid outlet 113b. The fluid outlet 113b is connected to the upper end of the heat transfer portion 141, and the lower end of the heat transfer portion 141 is connected to the heating portion 123 provided at the X-ray detector assembly 120.

The heat transfer portion 141 may be formed in the shape of a pipe allowing the fluid having absorbed the heat to pass therethrough. The heat transfer portion 141 may be formed of an insulating material or may be insulated such that the fluid does not lose heat while passing through the heat transfer portion 141. In addition, the heat transfer portion 141 may be formed of a flexible material so as to be easily connected to the housing 113 and the heating portion 123, and easily mounted in the frame 103.

The X-ray detector assembly 120 includes an X-ray detector 121 to detect X-rays transmitted through the object, such as the breast 30, and a heating portion 123 to contact the breast 30 in order to apply heat to the breast 30. As described above, the fluid which has absorbed heat produced in the X-ray tube 111, i.e., the heated fluid, is introduced into the heating portion 123 through the heat transfer portion 141. When the heated fluid circulates in the heating portion 123, the surface of the heating portion 123 is heated. Therefore, the patient will feel warm when their breast 30 contacts the heating portion 123. To this end, the heating portion 123 may be formed of a material having a high heat conduction quality. The structure of the heating portion 123 will be described in detail later.

Typically, the X-ray detectors are classified according to materials thereof, conversion techniques used to convert the detected X-rays into an electrical signal, and techniques for acquisition of an image signal.

First, the X-ray detectors are divided into a homogeneous type configured with homogeneous elements and a heterogeneous type configured with heterogeneous elements.

In the case that the X-ray detector is configured with homogeneous elements, the portion which detects X-rays in order to generate an electrical signal and the portion to read and process the electrical signal are constructed of semiconductors of the same material, or manufactured in a single process. For example, the X-ray detector may be composed of charge coupled devices (CCDs), as light-receiving elements, or complementary metal oxide semiconductors (CMOSs).

In the case that the X-ray detector is composed of heterogeneous elements, the portion which detects X-rays in order to generate an electrical signal and the portion to read and process the electrical signal are constructed of different materials, or manufactured in different processes. In one example, a light-receiving element such as a photodiode or Cadmium Zinc Telluride (CdZnTe) sensor is used to detect X-rays, while a CMOS readout integrated circuit (CMOS ROIC) is used to read and process an electrical signal. In another example, a strip detector is used to detect X-rays, while the CMOS ROIC is used to read and process an electrical signal. In a further example, X-rays are detected using an amorphous silicon (a-Si) or amorphous selenium (a-Se) flat panel system.

In addition, the X-ray detectors are divided into a direct conversion type and an indirect conversion type depending on the conversion techniques used to convert the X-rays into an electrical signal.

In the direct conversion technique, when X-rays are emitted onto a light-receiving element, electron-hole pairs are temporarily generated in the light-receiving element. Holes move toward the anode, and electrons toward the cathode, due to the electric field applied to both ends of the light-receiving element. The X-ray detector converts these movements into an electrical signal. In the direct conversion technique, the materials used for the light-receiving element include a-Se, CdZnTe, mercury iodide ($HgI_2$), and lead iodide ($PbI_2$).

In the indirect conversion technique, a scintillator is provided between the light-receiving element and the X-ray source. When photons with wavelengths in the range of visible light are produced through reaction between the X-rays emitted from the X-ray source and the scintillator, the light-receiving element senses the photons and converts the photons into an electrical signal. The materials used for the light-receiving element adopting the indirect conversion technique include a-Si. In addition, as the scintillator, a thin film-shaped gadolinium oxysulfide (Gadox) scintillator and a micro-column-shaped or needle-shaped thallium doped cesium iodide (CSI(T1)) scintillator may be used.

In addition, depending on the technique use for acquiring an image signal, the X-ray detectors are divided into a charge integration mode and a photon counting mode. In the charge integration mode, charges are stored for a certain period of time and then a signal is acquired from the charges. In the photon counting mode, whenever a signal is produced by a single X-ray photon, photons having an energy value equal to or higher than a threshold energy value are counted.

Any of the above techniques are applicable to the X-ray imaging apparatus 100 of the illustrated exemplary embodiment in order to implement the X-ray detector 121. Moreover, exemplary embodiments are not limited to the above techniques. Other techniques in which X-rays are detected and converted into an electrical signal in order to acquire an image signal are also applicable.

Hereinafter, the structure of an X-ray detector 121 employing the direct conversion technique of directly acquiring an electrical signal from X-rays and a hybrid technique of combining a light-receiving element for detection of X-rays with a read circuit chip will be described in detail.

Referring to FIG. 5B, the X-ray detector 121 includes a light-receiving element 121-1 to detect X-rays and convert the detected X-rays into an electrical signal, and a read circuit 121-2 to read an electrical signal. Herein, the read circuit 121-2 is configured in the form of a two-dimensional pixel array including a plurality of pixel areas. The light-receiving element 121-1 may be made of single-crystal semiconductor materials in order to secure a high resolution, fast response time and high dynamic range with a lower energy and lower doses of radiation. The single-crystal semiconductor materials include germanium (Ge), cadmium telluride (CdTe), cadmium zinc telluride (CdZnTe), and gallium arsenide (GaAs).

The light-receiving element 121-1 may be a PIN photodiode formed by joining a p-type layer 121-1c configured as a two-dimensional array of p-type semiconductors to an n-type semiconductor substrate 121-1b having a high resistance. The read circuit 121-2 employing a CMOS process is connected to the light-receiving element 121-1 for each pixel. The CMOS read circuit 121-2 and the light-receiving element 121-1 may be connected to each other through flip chip bonding. The CMOS read circuit 121-2 and the light-receiving element 121-1 may be connected to each other by forming a bump 121-3 of solder (PbSn) and indium (In). Reflow soldering may be performed by pressing the CMOS read circuit 121-2 and the light-receiving element 121-1 against each other and applying heat. The structure described above is simply an exemplary embodiment of the X-ray detector 121, and exemplary embodiments are not limited thereto.

Although not shown in the drawings, an X-ray grid to prevent scattering of X-rays may be located at the front of the X-ray detector 121. The front of the X-ray detector 121 is the side which first receives the X-rays.

As described above, the X-ray detector 121 includes devices such as semiconductors, and therefore the X-ray detector 121 needs to be maintained at a low temperature suitable for the properties of the devices. Accordingly, the heat dissipated from the heating portion 123 needs to be prevented from being transferred to the X-ray detector 121. To this end, the X-ray detector assembly 120 may further include a thermal insulation member 125 located between the heating portion 123 and the X-ray detector 121 to block the transfer of heat to the X-ray detector 121. Blocking the heat may be performed by absorbing or reflecting the heat.

For example, the thermal insulation member 125 may be a thermal insulation film coated with a thermal insulation material. The thermal insulation film may be formed by coating a synthetic resin film, a base film, such as a polyethylene terephthalate (PET) film with a thermal insulation material. Alternatively, a coated layer which blocks heat may be formed by directly applying a material having a thermal insulation property to the surface of the X-ray grid or the X-ray detector 121.

The thermal insulation member 125 is positioned at the front of the X-ray detector 121, and allows the X-rays transmitted through the breast 30 to be transmitted therethrough. Therefore, the thermal insulation material constructing the thermal insulation member 125 may be selected from among materials that do not block transmission of X-rays. For example, the thermal insulation material may be selected among materials allowing electromagnetic radiation having a wavelength between 0.001 nm and 10 nm to be transmitted therethrough. In addition, in the case that the X-ray blocking rate of the thermal insulation member 125 is unignorable, it may be possible to cancel the effect of the thermal insulation member 125 by correcting the X-ray image.

Once the breast 30 is positioned on the heating portion 123 when in order to perform X-ray imaging, and the compression paddle 131, which is vertically movable along the frame 103, compresses the breast 30 to make the thickness of the breast 30 suitable for X-ray imaging. The compression paddle 131 may be manually moved by a user or automatically moved according to preset values. In the illustrated exemplary embodiment, the user may be medical staff including a doctor, a radiology technologist and a nurse who may use the X-ray imaging apparatus 100 to examine the subject or patient. However exemplary embodiments are not limited thereto. The user may be anyone who uses the X-ray imaging apparatus 100.

The heating portion 123 is filled with the heated fluid. Accordingly, the heating portion 123 may keep the breast 30 warm while X-ray imaging is performed and may therefore reduce the level of discomfort felt by the subject.

Figure 6A:
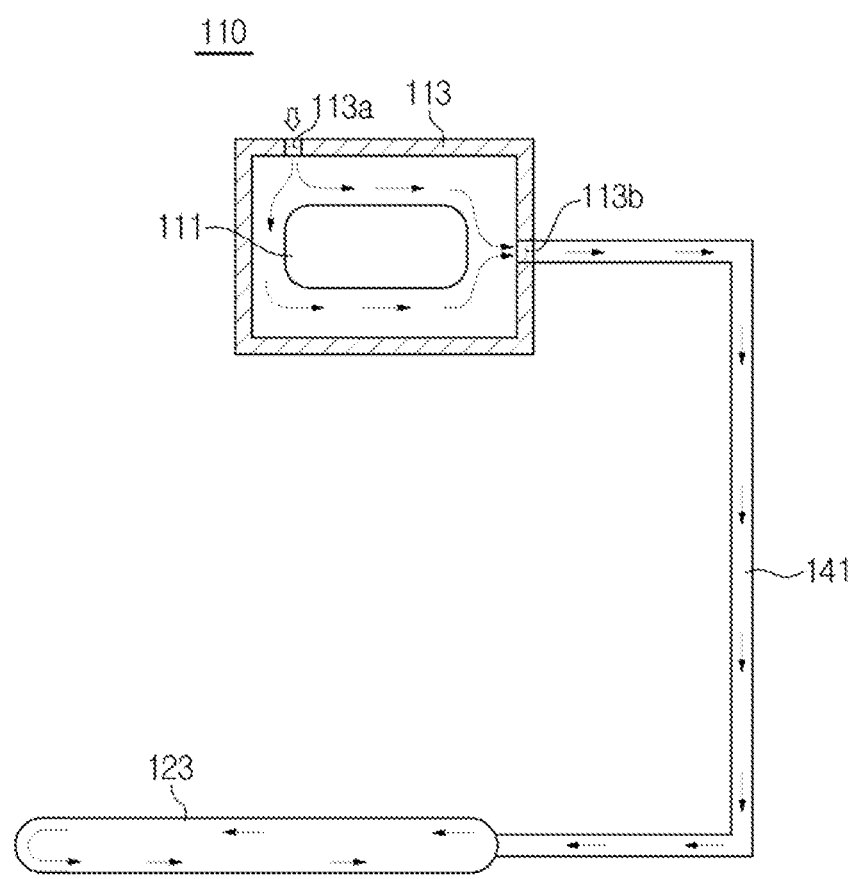
FIG. 6A is a view schematically illustrating heat transfer from an X-ray source to a heating portion.
Figure 6B:
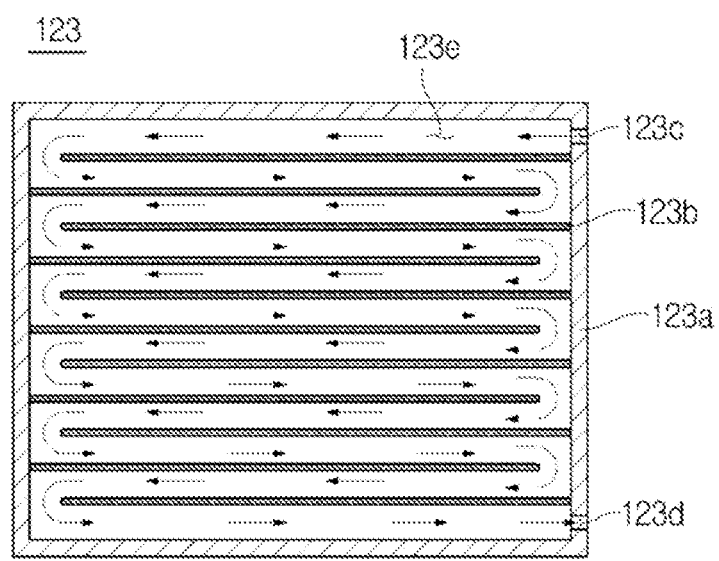
FIG. 6B is a view schematically illustrating the structure of a heating portion according to an exemplary embodiment.

FIG. 6A is a view schematically illustrating heat transfer from an X-ray source to a heating portion, and FIG. 6B is a view schematically illustrating the structure of a heating portion according to an exemplary embodiment.

FIG. 6A schematically shows only the structures involved in heat transfer from the heating portion 123 among the structures included in the X-ray source 110 and the X-ray detector assembly 120.

Referring to FIG. 6A, fluid is introduced through the fluid inlet 113a. The fluid absorbs heat dissipated from the X-ray tube 111 while passing through the housing 113. In the case that the fluid is for example, air, a hole may be formed in the X-ray source 110 to allow air to be introduced through the hole and the fluid inlet 113a. In the case that the fluid is for example, cooling water or cooling oil, a chamber to store the cooling water or cooling oil may be arranged at the outside of or inside of the X-ray source 110 to supply the fluid into the housing 113. To ensure smooth movement of the fluid, a fan may be provided in the housing 113.

While the housing 113 is illustrated in FIG. 6A as surrounding the entire X-ray tube 111, a portion of the X-ray tube 111 corresponding to the window 111i may be exposed outside of the housing 113 to prevent absorption of X-rays by the fluid. In the case that the housing 113 surrounds the whole X-ray tube 111 as shown in FIG. 6A, the whole housing 113 or the portion corresponding to the window 111i of the X-ray tube 111 may be constructed of a material that does not affect transmission of the X-rays, i.e., a material which does not absorb the X-rays.

The fluid which has absorbed the heat dissipated from the X-ray tube 111 flows into the heating portion 123 through the heat transfer portion 141. The outer cover 123a of the heating portion 123 is provided with a fluid inlet 123c through which the heated fluid is introduced, as shown in FIG. 6B. Once introduced, the fluid heats the surface of the heating portion 123, while circulating in the heating portion 123. That is, the surface of the heating portion 123 is heated by the fluid circulating in the heating portion 123, and thereby the breast 30 is heated during imaging. Accordingly, the heating portion 123 may be heated and perform heating at the same time.

When the circulation path of the fluid in the heating portion 123 is elongated, the efficiency of transferring heat to the surface of the heating portion 123 increases. To elongate the circulation path of the fluid, a plurality of partition walls 123b may be provided in the heating portion 123, and a passage 123e having a plurality of curved portions is formed in the heating portion 123 by the partition walls 123b.

For example, as shown in FIG. 6B, the partition walls 123 may be arranged in an interdigitated pattern, and the passage formed by the partition walls 123b may have a zigzag pattern.

The outer cover 123a corresponding to the end of the passage is provided with a fluid outlet 123d through which the fluid is discharged. After completing circulation, the fluid may be discharged through the fluid outlet 123d or re-introduced into the X-ray source 110.

In FIG. 6B, the partition walls 123b form the circulation passage 123e through which the fluid flows in the heating portion 123. However, this is merely an example and the exemplary embodiments are not limited to this example. Alternatively, a circulation pipe through which the heated fluid flows may be mounted in the heating portion 123.

Since the heating portion 123 needs to heat the breast 30 contacting the surface of the heating portion 123, the outer cover 123a may be formed of a material having high thermal conductivity. For example, the outer cover 123a may be formed of a synthetic resin or rubber.

Alternatively, the upper surface of the outer cover 123a that contacts the breast 30 may be formed of a thermally conductive material, and the lower surface of the outer cover 123a facing the X-ray detector 121 may be formed of a thermal insulation material. Therefore, the breast 30 is heated, while heat is not transferred to the X-ray detector 121.

Figure 7A:
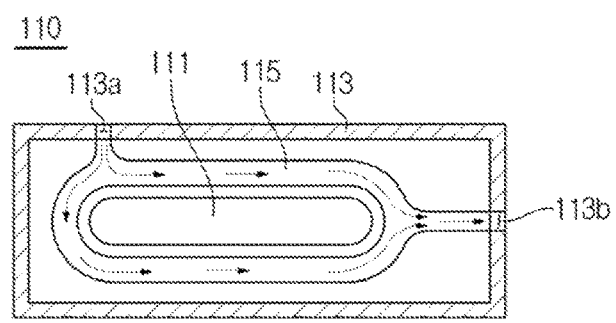
FIG. 7A is a view schematically illustrating an exemplary structure of the X-ray source which discharges heat.
Figure 7B:
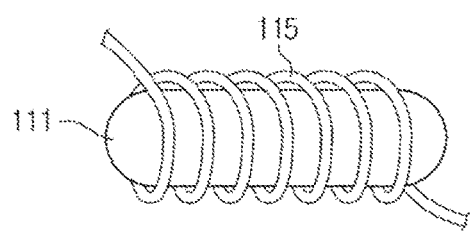
FIG. 7B is a view schematically illustrating another exemplary structure of the X-ray source which discharges heat.

FIG. 7A is a view schematically illustrating an exemplary structure of the X-ray source which discharges heat, FIG. 7B is a view schematically illustrating another exemplary structure of the X-ray source which discharges heat.

Referring to FIG. 7A, in order for the fluid to effectively absorb heat, the X-ray source 110 may be provided with an absorption pipe 115 which surrounds the X-ray tube 111. One end of the absorption pipe 115 may be connected to the fluid inlet 113a of the housing 113, while the other end of the absorption pipe 115 may be connected to the fluid outlet 113b. To increase the contact area between the fluid introduced through the fluid inlet 113a and the X-ray tube 111, the absorption pipe 115 may be branched into at least two portions, and the branched portions of the absorption pipe 115 may join near the fluid outlet 113b.

Accordingly, the fluid introduced through the fluid inlet 113a absorbs heat dissipated from the X-ray tube 111 while flowing along the absorption pipe 115. Then, the fluid is discharged through the fluid outlet 113b and introduced into the heating portion 123 through the heat transfer portion 141.

While the absorption pipe 115 is illustrated in FIG. 7A as surrounding the upper and lower portions of the X-ray tube 111, the absorption pipe 115 may be formed to surround the lateral surface of the X-ray tube 111 or the lateral surface and upper portion of the X-ray tube 111 such that the window 111i formed at the lower portion of the X-ray tube 111 is not covered.

The inner space of the housing 113 may be filled with a refrigerant such as cooling oil, cooling water or air in addition to the fluid which flows through the fluid inlet 113a and the fluid outlet 113b. Although not shown in FIG. 7A, an inlet and outlet through which the refrigerant, which fills the housing 113, flows may be separately provided.

Alternatively, since the X-ray tube 111 may be cooled by the fluid passing through the absorption pipe 115, the housing 113 which is filled with a separate refrigerant may be omitted.

In another example of increasing the heat absorption efficiency of the fluid, the absorption pipe 115 may have a spiral shape which surrounds the X-ray tube 111 as shown in FIG. 7B. However, this is merely an exemplary embodiment and there is no limit as to the shape of the absorption pipe 115. The absorption pipe 115 provided to the X-ray source 110 may have various shapes other than the shapes shown in FIGS. 7A and 7B.

Figure 8:
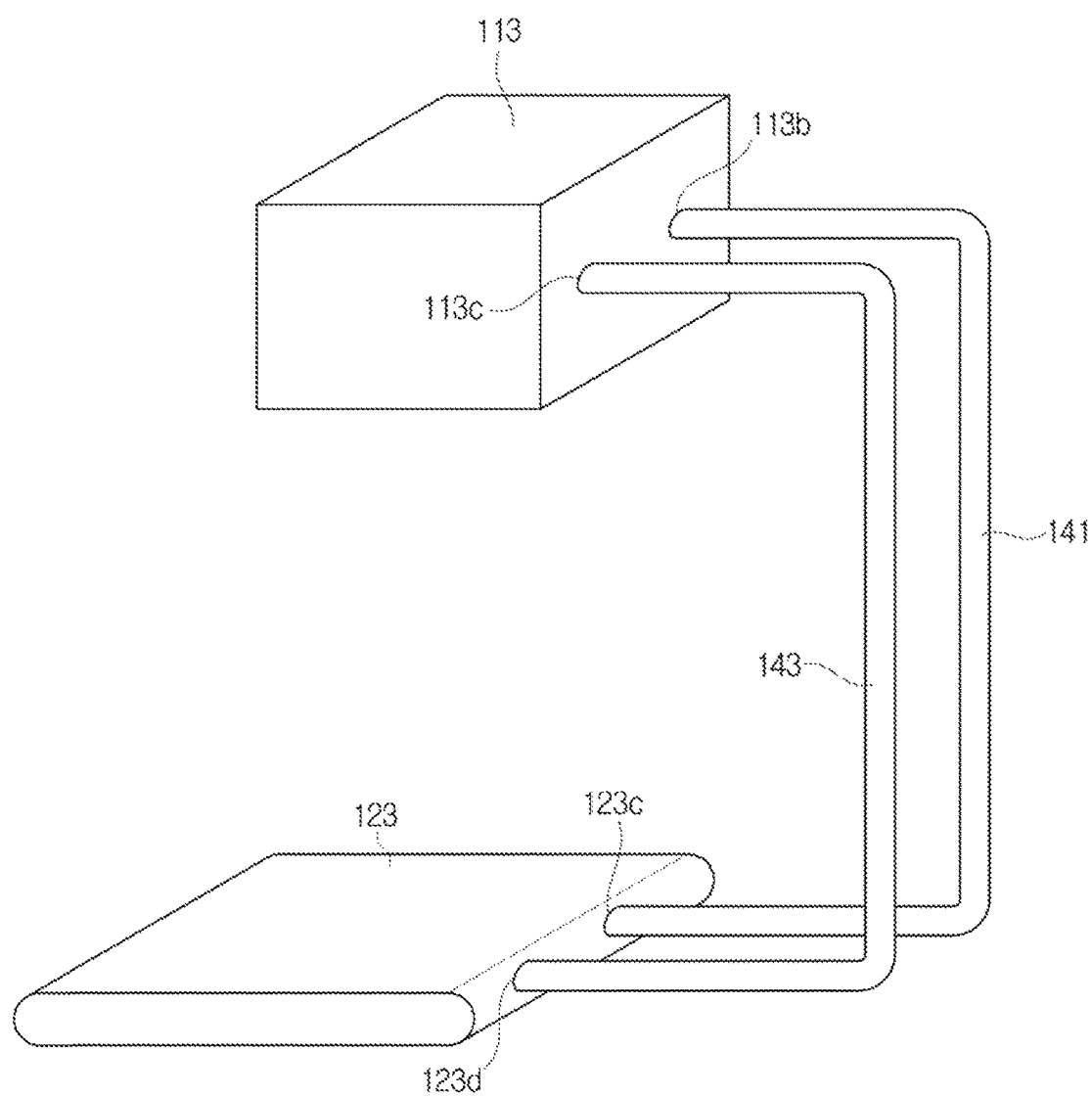
FIG. 8 is a view schematically illustrating a structure which allows a fluid circulating in a heating portion to return to the X-ray source.

FIG. 8 is a view schematically illustrating a structure which allows a fluid circulating in a heating portion to return to the X-ray source.

As described above in FIG. 6B, the heating portion 123 is provided with a fluid outlet 123d through which the fluid having circulated in the heating portion 123 is discharged. The X-ray imaging apparatus 100 may further include a fluid transport portion 143 to transport the discharged fluid to the X-ray source 110. The fluid introduced into the heating portion 123 loses heat during circulation in the heating portion 123 and thus the temperature thereof is lowered. Since the fluid discharged through the fluid outlet 123d may function as the refrigerant, the fluid may be introduced into the housing 113 through the fluid transport portion 143.

To this end, the housing 113 may be provided with a fluid inlet 113c. To distinguish the fluid inlet 113c from the fluid inlet 113a through which the fluid is introduced from an outside, the fluid inlet 113c, which is connected to the fluid transport portion 143, is identified as a second fluid inlet, and the fluid inlet 113a is identified as a first fluid inlet. The fluid introduced through the second fluid inlet 113c may absorb heat dissipated from the X-ray tube 111 while circulating in the housing 113. The structure shown in FIG. 8 is still applicable in the case where the absorption pipe 115 is provided in the housing 113, as described above with reference to FIGS. 7A and 7B.

Figure 9:
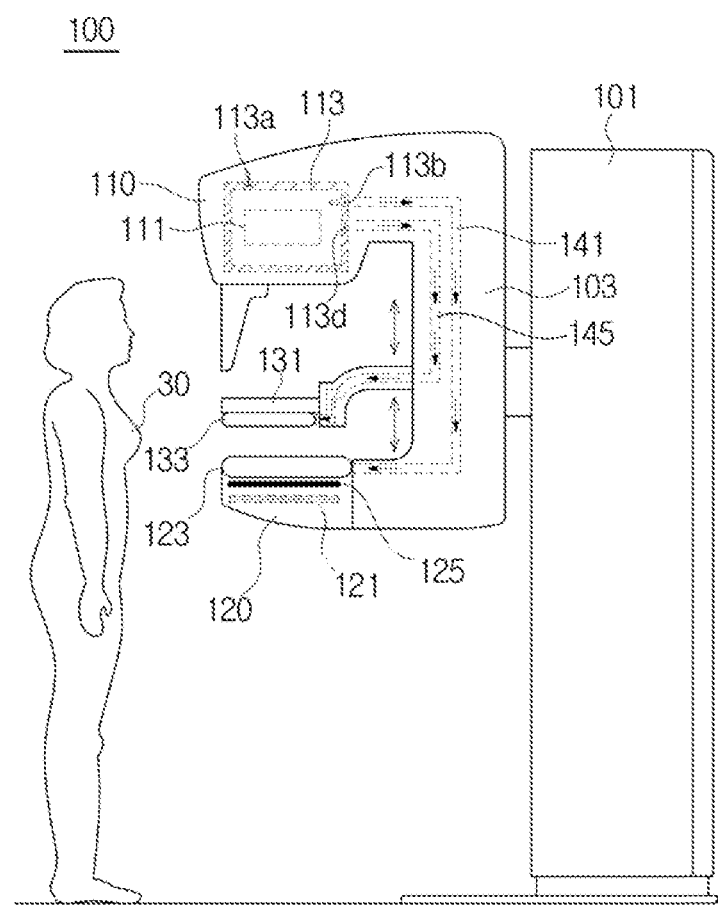
FIG. 9 is a view schematically showing an external appearance of an X-ray imaging apparatus provided with a second heating portion mounted on the lower portion of the compression paddle.

FIG. 9 is a view schematically showing an external appearance of an X-ray imaging apparatus provided with a second heating portion mounted on the lower portion of the compression paddle.

As described above, the compression paddle 131 compresses the object, such as a breast 30, to capture an X-ray image of the breast. Accordingly, the lower part of the breast contacts the heating portion 123, and the upper part of the breast contacts the lower portion of the compression paddle 131. The X-ray imaging apparatus 100 may further include a heating portion 133 mounted on the lower portion of the compression paddle 131 to heat not only the upper part but also the lower part of the breast, as shown in FIG. 9. Since there is a heating portion 123 mounted on the lower portion of the compression paddle 131, the heating portion 123 which contacts the lower part of the breast 30 is identified as a first heating portion, and the heating portion 133 which contacts the upper part of the breast 30 is identified as a second heating portion.

Heat supplied to the second heating portion 133 may also be waste heat produced by the X-ray source 110. The X-ray source 110 and the second heating portion 133 are connected to each other by a heat transfer portion 145 which transfers heat from the X-ray source 110 to the second heating portion 133. To distinguish the heat transfer portion 145 from the heat transfer portion 143 which transfers heat from the X-ray source 110 to the first heating portion 123, the heat transfer portion 141 is identified as a first heat transfer portion, and the heat transfer portion 145 is identified as a second heat transfer portion.

The description of the first heating portion 123 given above is applicable to the second heating portion 133, and the description of the first heat transfer portion 141 is applicable to the second heat transfer portion 145.

The upper end of the second heat transfer portion 145 may be connected to a fluid outlet 113d provided in the housing 113 as shown in FIG. 9, or may branch out from the first heat transfer portion 141. The fluid outlet 113d connected to the second heat transfer portion 145 is identified as a second fluid outlet 113d, and the fluid outlet 113b connected to the first heat transfer portion 141 is identified as a first fluid outlet 113b.

Figure 10:
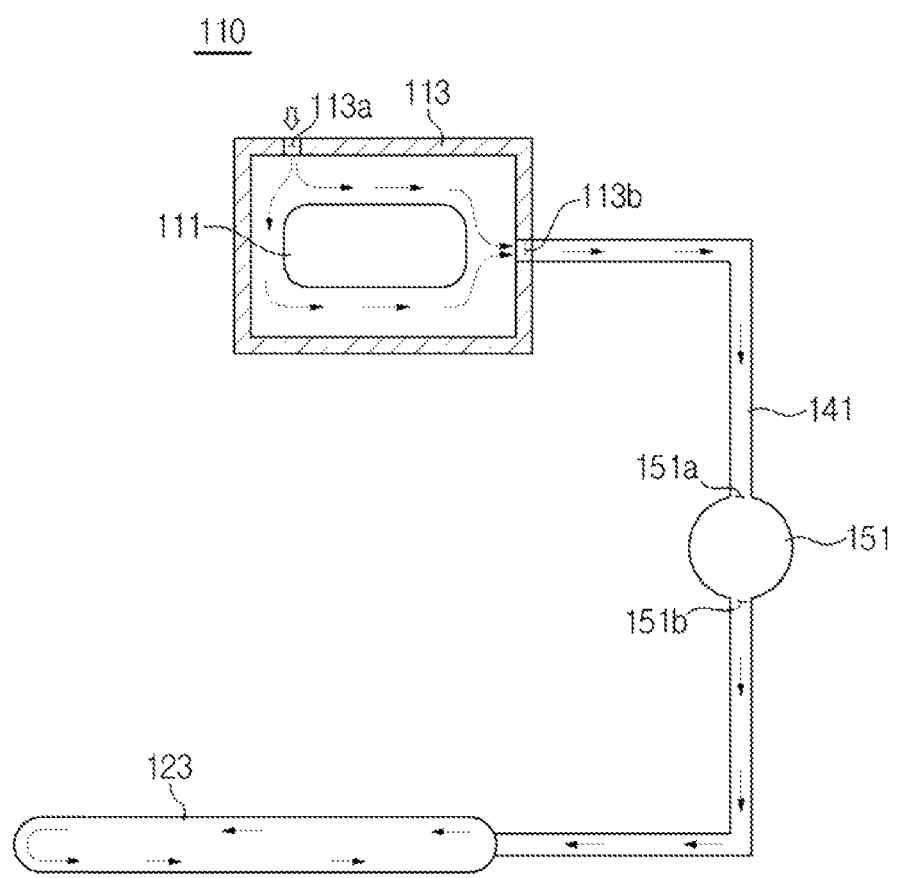
FIG. 10 is a view schematically illustrating a structure in which heat produced by the X-ray source may be stored.

FIG. 10 is a view schematically illustrating a structure in which heat produced by the X-ray source may be stored.

Heat produced by the X-ray source 110 may be used to immediately heat the breast 30. However, to more efficiently heat the breast 30, the X-ray imaging apparatus 100 may further include a heat storage portion 151 to store the heat produced by the X-ray source 110, as shown in FIG. 10.

Specifically, production of heat by the X-ray source 110 occurs when X-rays are generated when performing X-ray imaging. Accordingly, by storing the heat produced during the X-ray imaging in the heat storage portion 151 and using the heat stored in the heat storage portion 151 when subsequent X-ray imaging is performed, the heating portion 123 may be heated before X-ray imaging begins, and the heating portion 123 may also be efficiently heated during the operation of X-ray imaging. The heating storage portion 151 can also be used to heat the second heating portion 133.

The heat storage portion 151 may be realized as a chamber which is capable of storing the fluid, as shown in FIG. 10. The heat storage portion 151 stores the fluid having absorbed heat dissipated from the X-ray tube 111, and when the heating portion 123 needs to be heated, it supplies the stored fluid to the heating portion 123. The heat storage portion 151 may be formed in the middle of the heat transfer portion 141 as shown in FIG. 10, or may be formed in the housing 113 or between the absorption pipe 115 and the upper end of the heat transfer portion 141. The heat storage portion 151 may be formed of a thermal insulation material or covered by insulation so as to retain the heat of the fluid stored therein. Further, the heat storage portion 151 includes an inlet 151a and an outlet 151b.

Due to the structure described above, the X-ray imaging apparatus 100 may appropriately control the flow of heat transferred from the X-ray source 110 to the heating portion 123 to maintain an optimum temperature of the heating portion 123. A detailed description is given below.

Figure 11:
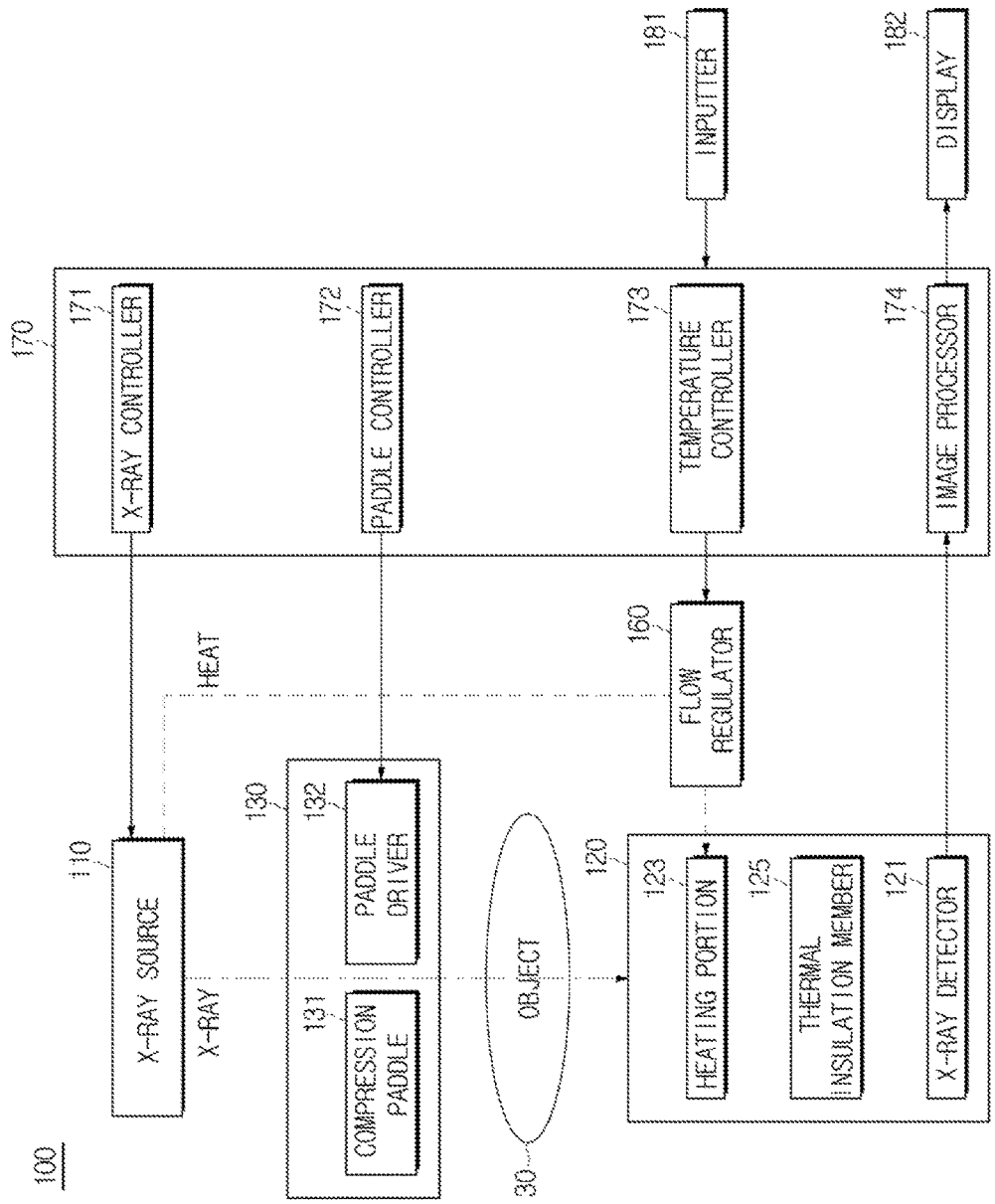
FIG. 11 is a control block diagram illustrating an X-ray imaging apparatus according to an exemplary embodiment.

FIG. 11 is a control block diagram illustrating an X-ray imaging apparatus according to an exemplary embodiment.

Referring to FIG. 11, the X-ray imaging apparatus 100 includes a flow regulator 160 which regulates the flow of heat transferred from the X-ray source 110 to the heating portion 123, and a controller 170 which controls the operation of the X-ray imaging apparatus 100, in addition to the X-ray source 110, the X-ray detector assembly 120 and the compression paddle 131, which are described above.

As described above, heat produced by the X-ray source 110 may be transferred to the heating portion 123 through the fluid functioning as a medium. The flow regulator 160 may be realized as a member which regulates the flow of the fluid such as a valve, a fan, and a pump. The details of the configuration of the flow regulator 160 will be described later.

The controller 170 includes an X-ray controller 171 which controls the generation of X-rays, a paddle controller 172 which controls the movement of the compression paddle 131, a temperature controller 173 which controls the flow regulator 160, and an image processor 174 which processes an electrical signal transmitted from the X-ray detector 121 to produce an X-ray image of the breast 30.

The X-ray controller 171 may control conditions for X-ray imaging including the tube voltage and tube current of the X-ray tube 111, the X-ray exposure time, the type of filter, the target material, the focal spot size, and the emission range of area. The X-ray controller 171 may perform auto exposure control by automatically controlling the X-ray imaging conditions, or may perform control operations according to control commands input through an inputter 181 by the user.

As described above, the compression paddle 131 may automatically move. In the case that the compression paddle 131 automatically moves, the paddle controller 172 may transmit a control signal to a paddle driver 132, which drives the compression paddle 131, which causes the compression paddle 131 to move. The paddle driver 132 may include a motor to provide power to the compression paddle 131. The compression paddle 131 and the paddle driver 132 constitute a paddle assembly 130. Movement of the compression paddle 131 may be automatically adjusted according to predetermined values or the properties of the breast 30. For example, in the case that the required thickness of the breast 30 for X-ray imaging is set to 5 cm, the paddle controller 172 may transmit a control signal to a paddle driver 142 to move a compression paddle 141 to a position 5 cm away from the X-ray detector assembly 120.

The temperature controller 173 controls the temperature of the heating portion 123 by controlling the flow regulator 160. For example, in the case that the flow regulator 160 is a fan or a pump, the fan or pump may be driven to direct the flow of the fluid toward the heating portion 123 so as to increase the temperature of the heating portion 123. In addition, the temperature controller 173 may stop or reversely operate the flow regulator 160 to lower the temperature of the heating portion 123. In the case that the flow regulator 160 is a valve, the temperature of the heating portion 123 may be increased by opening the flow regulator 160, and may be lowered by closing the flow regulator 160. In the case that the degree of the opening of the valve is adjustable, the amount of fluid flowing to the heating portion 123 may be adjusted by adjusting the degree of the opening of the valve.

Alternatively, the flow regulator 160 may include both the fan or the pump and the valve. In this case, the temperature controller 173 may control the operations of the fan or the pump and the valve to more precisely regulate the flow of the fluid. The X-ray imaging apparatus 100 also includes a display 182 which displays the status of heating the heating portion 123.

Figure 12A:
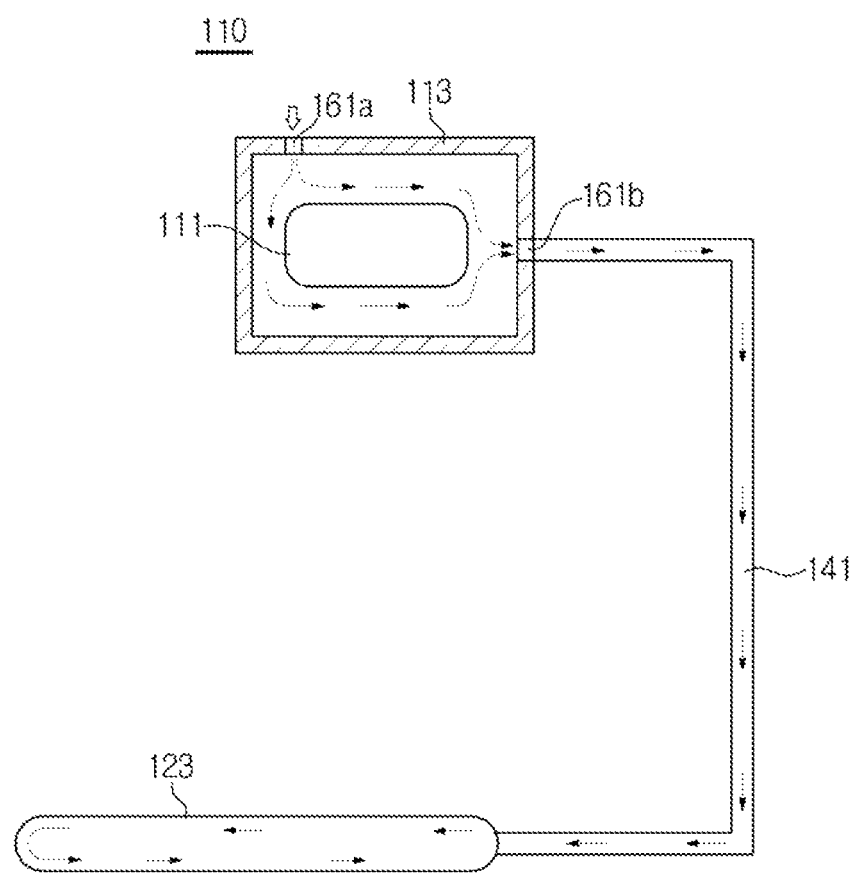
FIG. 12A is a view schematically illustrating flow of a fluid though a flow regulator mounted to a fluid inlet and fluid outlet formed in a housing.
Figure 12B:
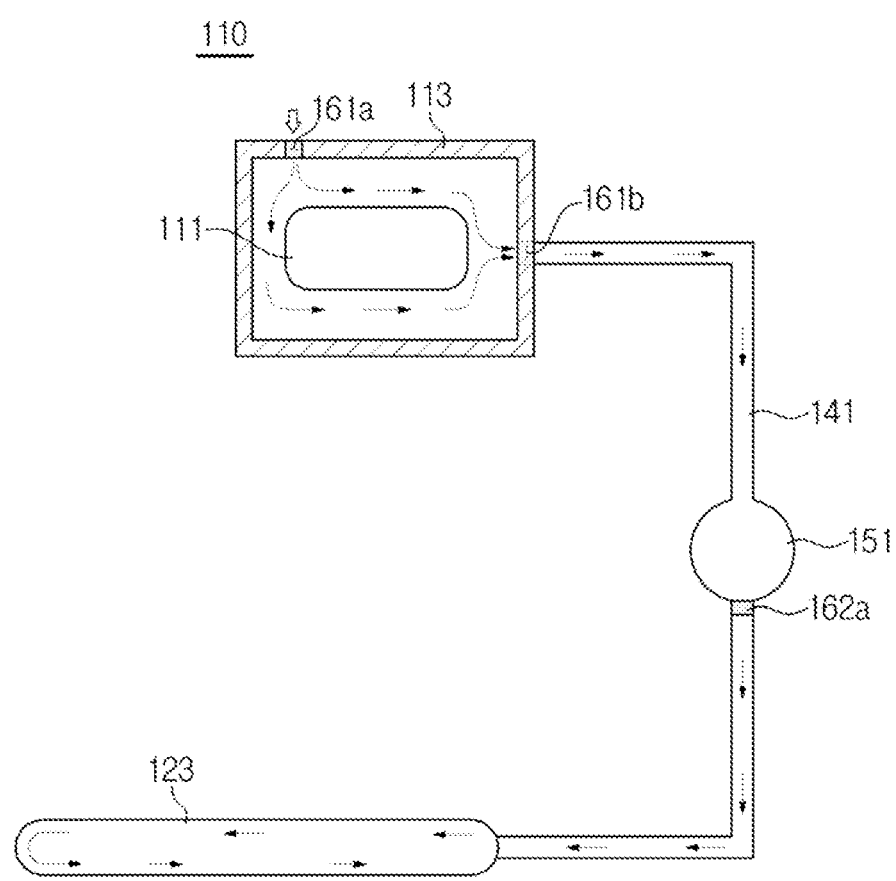
FIG. 12B a view schematically illustrating flow of a fluid with another flow regulator mounted to the outlet of the heat storage portion.

FIG. 12A is a view schematically illustrating flow of a fluid though a flow regulator mounted to a fluid inlet and fluid outlet formed in a housing, and FIG. 12B a view schematically illustrating flow of a fluid with another flow regulator mounted to the outlet of the heat storage portion.

Referring to FIG. 12A, valve 161a and valve 161b, are shown as the flow regulators and may be respectively mounted to the fluid inlet 113a of the housing 113 and the fluid outlet 113b or the upper end of the heat transfer portion 141. When the temperature controller 173 opens the valve 161a mounted to the fluid inlet 113a, the fluid is introduced into the housing 113 from outside of the housing 113, and the introduced fluid is heated, while circulating in the housing 113. When the temperature controller 173 opens the valve 161b mounted to the fluid outlet 113b or the upper end of the heat transfer portion 141, the heated fluid is supplied to the heating portion 123 through the heat transfer portion 141. The fan or the pump may be provided in the housing 113 to ensure a smoother flow of the fluid, and the temperature controller 173 may control the valve 161a and valve 161b and the fan or pump together.

The temperature controller 173 may open the valve 161b mounted to the fluid outlet 113b to heat the heating portion 123 when X-ray imaging begins. Alternatively, the temperature controller 173 may open the valve 161b mounted to the fluid outlet 113b to pre-heat the heating portion 123 before X-ray imaging begins. In the case that the heating portion 123 is pre-heated, the heat used in pre-heating may be the heat produced during the previous X-ray imaging.

In the case that the X-ray imaging apparatus 100 includes the heat storage portion 151, a valve 162a may also be mounted to an outlet 151b of the heat storage portion 151 as a flow regulator, as shown in FIG. 12B. Alternatively, a fan or pump may be provided in place of or together with the valve.

For example, part of or all of the heat produced during the X-ray imaging may be stored in the heat storage portion 151, and before subsequent X-ray imaging begins, the heated fluid may be supplied to the heating portion 123 by opening the valve 162a. Thus, the heating portion 123 may be pre-heated by the supplied fluid. Then, when X-ray imaging begins, heat dissipated from the X-ray source 110 may be transferred to the heat storage portion 151 through the fluid, a medium, by opening the valve 161a mounted to the fluid inlet 113a and the valve 161b mounted to the fluid outlet 113b. At this time, the temperature controller 173 may close the valve 162a or keep the valve 162a open so that part or all of the heat produced by the X-ray source 110 is directly transferred to the heating portion 123.

The flow regulator 160 may also be provided to the second fluid inlet 113c of FIG. 8 and the second fluid outlet 113d of FIG. 9.

Figure 13:
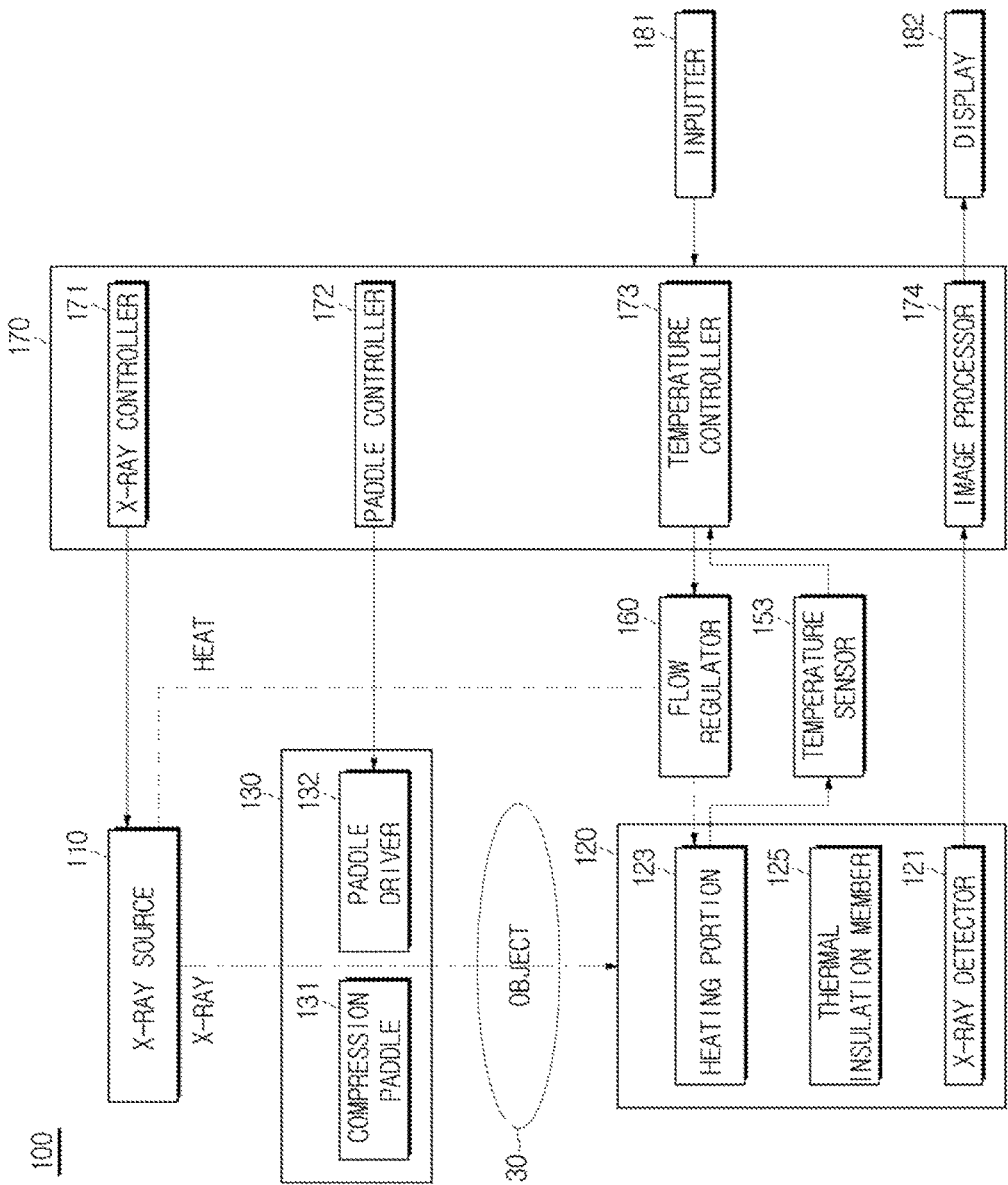
FIG. 13 is a control block diagram illustrating the X-ray imaging apparatus which includes a temperature sensor.

FIG. 13 is a control block diagram illustrating the X-ray imaging apparatus which includes a temperature sensor.

Referring to FIG. 13, the X-ray imaging apparatus 100 may further include a temperature sensor 153 to sense or measure the temperature of the heating portion 123. The temperature sensor 153 may be mounted to a portion of the heating portion 123 to sense the temperature of the heating portion 123. The temperature sensor 153 transmits the sensed temperature to the temperature controller 173, and the temperature controller 173 controls the flow regulator 160 based on the sensed or measured temperature.

For example, if the temperature sensed by the temperature sensor 153 exceeds a predetermined upper temperature limit, the temperature controller 173 may control the flow regulator 160 to decrease the amount of the fluid transferred to the heating portion 123. If the sensed temperature is lower than a predetermined lower temperature limit, the temperature controller 173 may control the flow regulator 160 to increase the amount of fluid transferred to the heating portion 123.

If another heating portion 133 is mounted to the lower portion of the compression paddle 131 as described above in FIG. 9, the temperature sensor 153 may also be mounted to a part of the heating portion 133 mounted on the compression paddle 131, and the temperature controller 173 may control the flow regulator 160 to regulate the temperature of the heating portion 133 mounted on the compression paddle 131.

Figure 14:
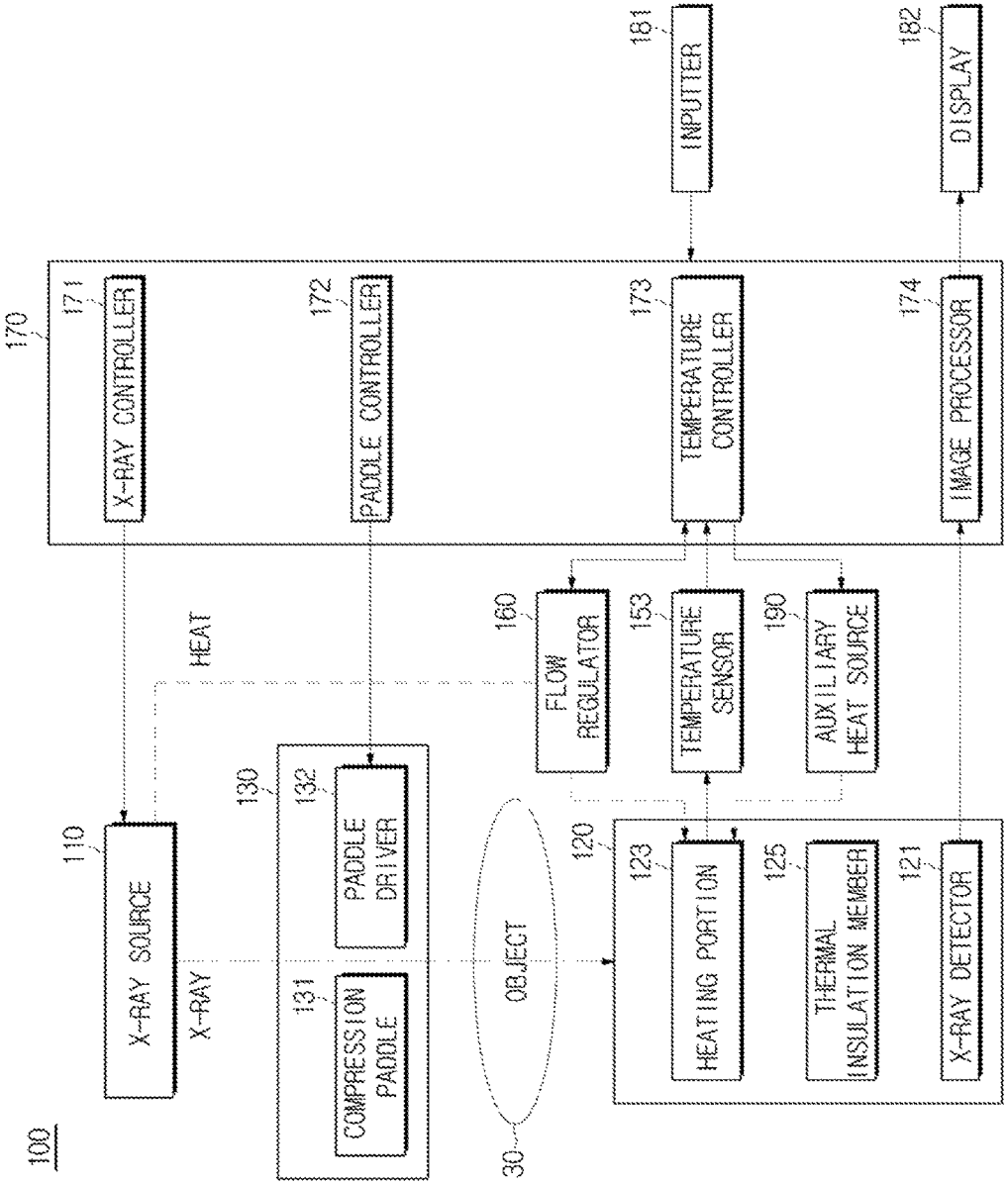
FIG. 14 is a control block diagram illustrating the X-ray imaging apparatus which includes an auxiliary heat source.

FIG. 14 is a control block diagram illustrating the X-ray imaging apparatus which includes an auxiliary heat source.

Referring to FIG. 14, the X-ray imaging apparatus 100 may further include a separate auxiliary heat source 190 to heat the heating portion 123. The auxiliary heat source 190 may supply heat to the heating portion 123 in various ways. The auxiliary heat source 190 may directly heat the surface of the heating portion 123, or heat the fluid introduced into the heating portion 123.

As described above, the main heat source of the X-ray imaging apparatus 100 is the X-ray tube 111. If the heat produced in the X-ray tube 111 is not sufficient to heat the heating portion 123, the temperature controller 173 turns on the auxiliary heat source 190 to supply supplementary heat. In the case that the X-ray imaging apparatus 100 remains unused for a certain amount of time, for example, when X-ray imaging is performed for the first time during a day, the amount of heat transmitted to the heating portion 123 may not be sufficient. In this case, the temperature controller 173 may turn on the auxiliary heat source 190 to supply heat to the heating portion 123.

A specific description will be given below of heating the heating portion 123 controlled by the temperature controller 173, with a day identified as an operation cycle of the X-ray imaging apparatus 100. Before X-ray imaging is performed for the first time during a day, the X-ray source 110 may be calibrated. At this time, the produced heat is stored in the heat storage portion 151, and the stored heat is transferred to the heating portion 123 to heat the surface of the heating portion 123 to perform the X-ray imaging. The heating portion 123 may be heated before the breast 30 comes into contact with the heating portion 123. The temperature sensor 153 senses the temperature of the heating portion 123 and delivers the temperature to the temperature controller 173. In the case that the temperature of the heating portion 123 is lower than a predetermined lower temperature limit, the temperature controller 173 may turn on the auxiliary heat source 190 to supply supplementary heat. Alternatively, in the case that the generation of X-rays is not performed for at least a certain amount time, the temperature controller 173 may turn on the auxiliary heat source 190 regardless of the sensed temperature.

In the case that X-ray imaging is being performed for the second time during the day, the heating portion 123 may be pre-heated before the breast 30 contacts the heating portion 123. To this end, the heat stored in the heat storage portion 151 during the previous X-ray imaging may be transferred to the heating portion 123, and the temperature sensor 153 senses the temperature of the heating portion 123. The heat may be stored and transferred through the fluid functioning as a medium. In the case that the sensed temperature exceeds the predetermined temperature limit, the temperature controller 173 may control the flow regulator 160 mounted on the heat storage portion 151 to decrease the amount of the fluid transferred to the heating portion 123.

The temperature sensor 153 may sense the temperature of the heating portion 123 in real time or at regular intervals. In the case that the temperature of the heating portion 123 is lower than a predetermined lower temperature limit, the temperature controller 173 controls the flow regulator 162a mounted to the outlet of the heat storage portion 151 to increase the amount of the fluid transferred to the heating portion 123. At this time, in the case that the amount of the fluid to be transferred to the heating portion 123 is insufficient, the temperature controller 173 may turn on the auxiliary heat source 190 to supplement heat supplied to the heating portion 123. To determine whether the amount of the fluid is insufficient, the heat storage portion 151 may be provided with a member to measure the amount of the fluid.

Figure 15:
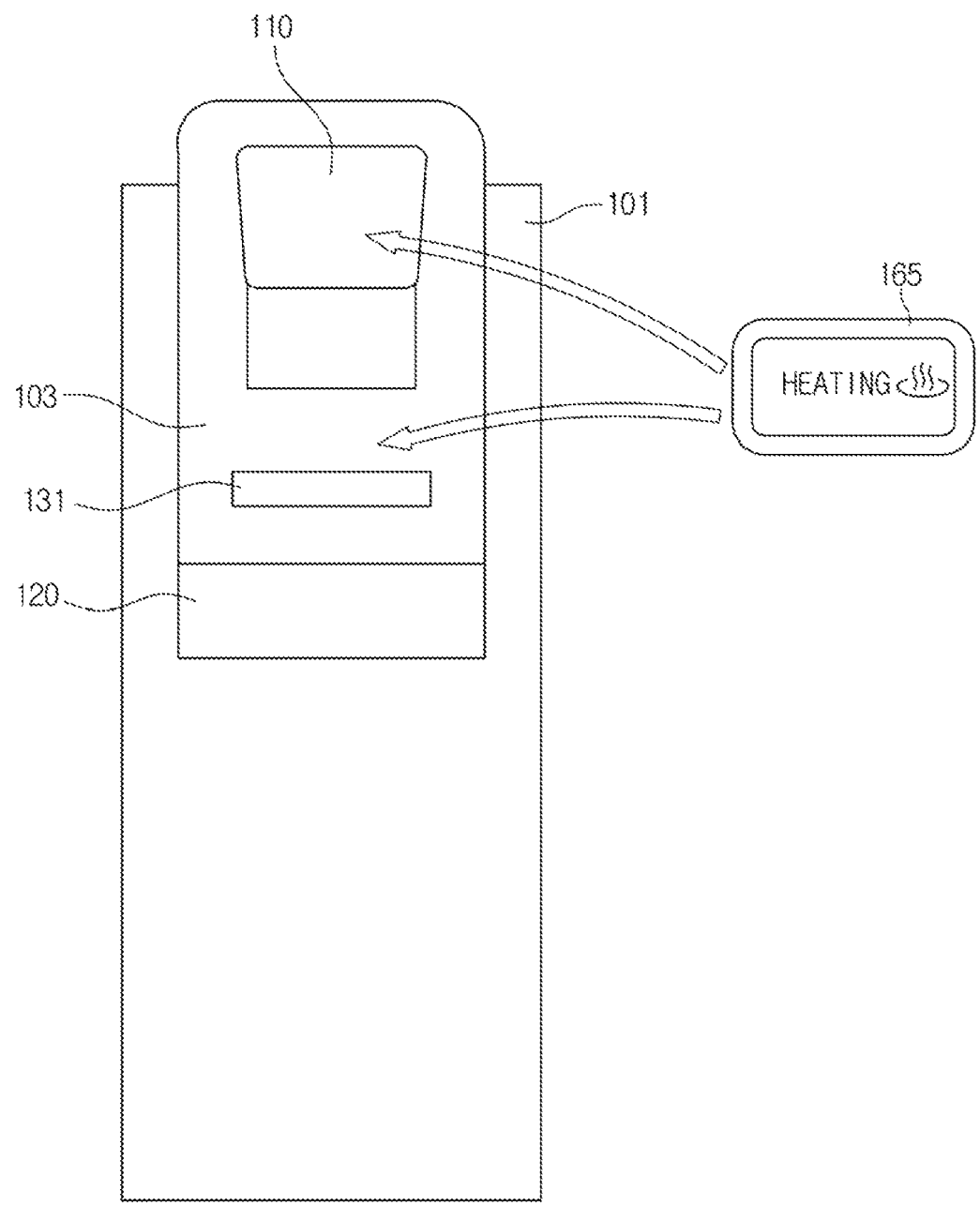
FIG. 15 is a view schematically showing an external appearance of an X-ray imaging apparatus which includes a display to display information indicating that the heating portion is being heated.

FIG. 15 is a view schematically showing an external appearance of an X-ray imaging apparatus including a display which displays information indicating that the heating portion is being heated.

FIG. 15 shows a view of the X-ray imaging apparatus 100 as seen by the patient. As shown in FIG. 15, a display 165, which displays information indicating that the heating portion 123 is being heated, may be mounted on a part of the X-ray imaging apparatus 100 which is visible by the patient. For example, the display 165 may be mounted on the front surface of the X-ray source 110 or the front surface of the frame 103. Further, the display apparatus can be, for example, a monitor which is controllable by the user. When information indicating that the heating portion 123 is being heated is displayed on the display 165 during the operation of X-ray imaging, the subject may be prevented from feeling anxious or discomfort from the cold since the X-ray imaging apparatus 100 is heated.

In the exemplary embodiments described above, the fluid functions as a medium through which heat produced in the X-ray tube 111 is transferred. However, exemplary embodiments are not limited thereto. For example, heat may be transferred by conduction. The X-ray tube 111 may be connected to the heating portion 123 using a metal wire having a high thermal conductivity, and a coil connected to the metal wire may be installed in the heating portion 123. A material having high thermal conductivity may be located adjacent to the X-ray source 110 in the X-ray tube 111 to absorb heat produced in the X-ray tube 111 and transfer the heat to the heating portion 123 through the metal wire.

Hereinafter, a control method for an X-ray imaging apparatus according to an exemplary embodiment will be described. The X-ray imaging apparatus 100 described above is applicable to the control method for an X-ray imaging apparatus.

Figure 16:
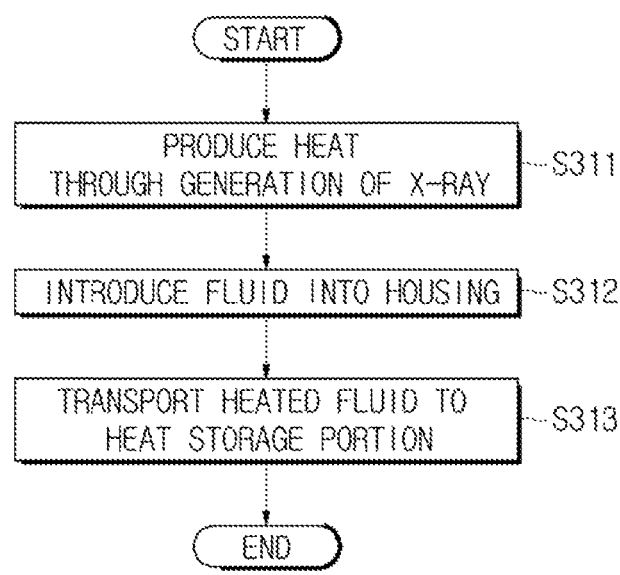
FIG. 16 is a flowchart illustrating the process of storing heat in a control method for an X-ray imaging apparatus according to an exemplary embodiment.

FIG. 16 is a flowchart illustrating the process of storing heat in a control method for an X-ray imaging apparatus according to an exemplary embodiment. In the illustrated exemplary embodiment, the fluid serves as a medium for transferring heat.

First, X-rays are generated to produce heat (S311). When electric power is applied to the X-ray tube 111 to generate X-rays, thermal electrons produced in the filament 111h of the cathode 111e strike the target material 111d of the anode. At this time, less than 1% of the energy of the electrons is converted into X-rays and the remainder of the energy is converted into heat. Thereby, heat is produced in the X-ray tube 111.

Then, the fluid is introduced into the housing 113 which surrounds the X-ray tube 111 (S312). To allow introduction of the fluid, the fluid inlet 113a formed in the housing 113 may be opened. The fluid may be air, cooling water or cooling oil. However, the types of the fluids are not limited as long as they are capable of absorbing and dissipating heat. The fluid introduced into the housing 113 is heated by absorbing heat dissipated from the X-ray tube 111. This operation is an example of the methods which cause the fluid to flow around the X-ray tube 111 to absorb the heat dissipated from the X-ray tube 111. Alternatively, the absorption pipe 115 through which the fluid flows may be located around the X-ray tube 111.

The heated fluid is transported to a heat storage portion (S313). For example, the heat storage portion 151 may be formed in the shape of a chamber in the middle of the heat transfer portion 141, which connects the X-ray source 110 with the heating portion 123. The heated fluid may be stored in the heat storage portion 151 by closing the valve 162a provided at the outlet 151b of the heat storage portion 151.

Figure 17:
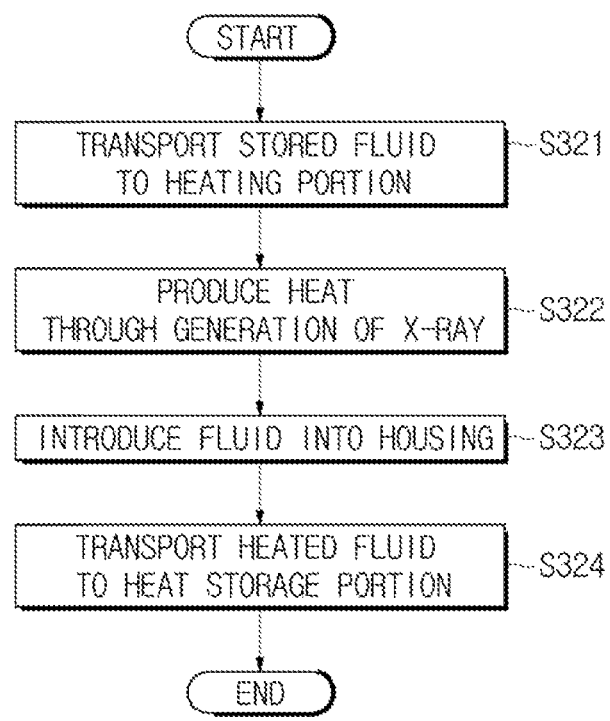
FIG. 17 is a flowchart illustrating the processes of heating and storing heat in a control method for an X-ray imaging apparatus according to an exemplary embodiment.

FIG. 17 is a flowchart illustrating the processes of heating and storing heat in a control method for an X-ray imaging apparatus according to an exemplary embodiment.

Referring to FIG. 17, the stored fluid is transported to the heating portion to perform X-ray imaging (S321). Transport of the fluid may begin before the breast 30 contacts the heating portion 123 to perform X-ray imaging. Once the stored fluid is transported to the heating portion 123, the fluid heats the surface of the heating portion 123 while circulating in the heating portion 123. Thereby, the breast 30 which contacts the heating portion 123 is also heated, and thus the subject may feel warm.

Then, when X-ray imaging begins, heat is produced due to generation of X-rays (S322). As described above, the fluid is introduced into the housing (S323), and the fluid heated by the heat dissipated from the X-ray tube 111 is transported to the heat storage portion (S324). At this time, if the heating portion 123 has been sufficiently heated, all the heated fluid may be stored in the heat storage portion 151 by closing the valve 162a provided at the outlet of the heat storage portion 151. If the heating portion 123 needs to be heated more, the valve 162a may be opened such that storage of heat and heating may be simultaneously performed.

Figure 18:
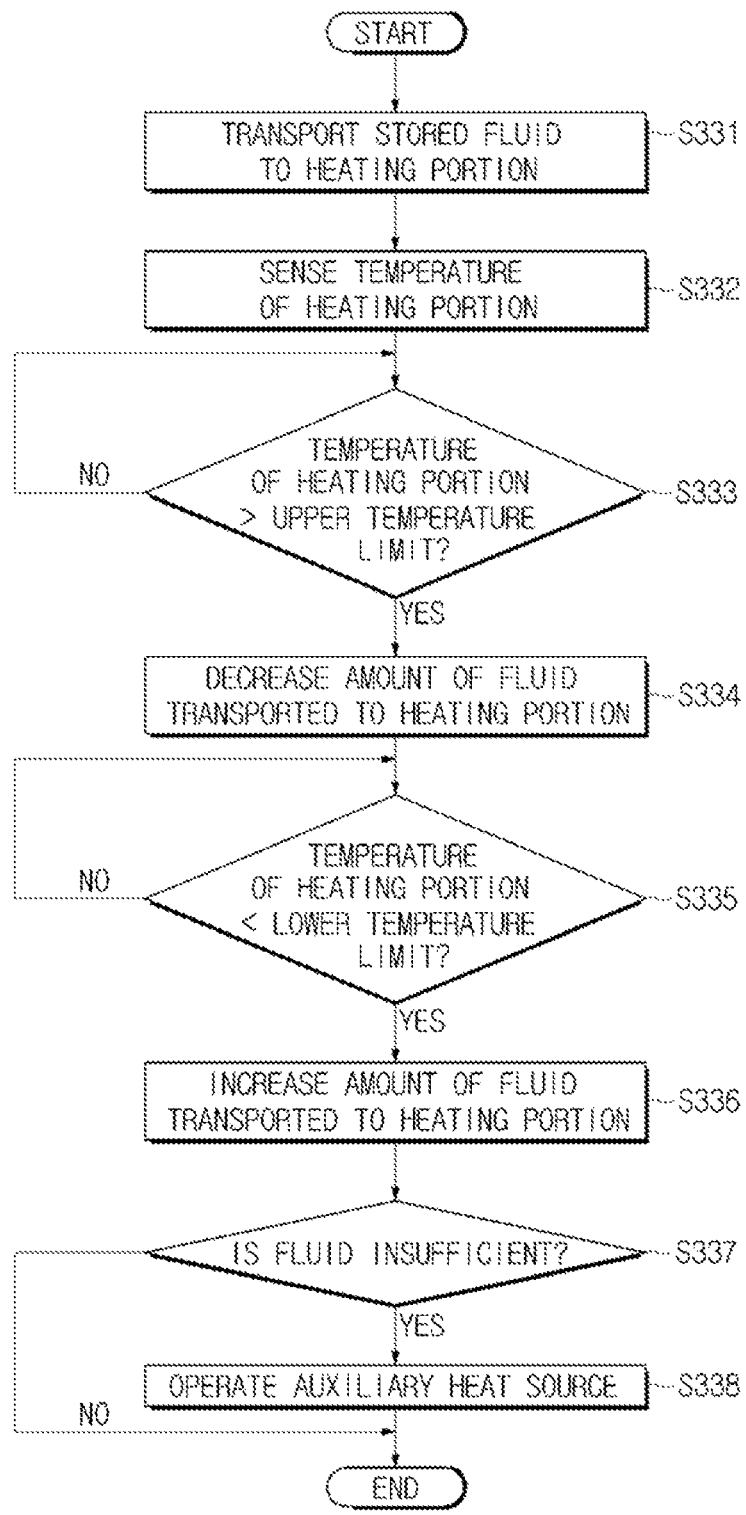
FIG. 18 is a flowchart illustrating the process of controlling heat transfer by sensing the temperature of a heating portion in a control method for an X-ray imaging apparatus according to an exemplary embodiment.

FIG. 18 is a flowchart illustrating the process of controlling heat transfer by sensing the temperature of a heating portion in a control method for an X-ray imaging apparatus according to an exemplary embodiment.

Referring to FIG. 18, the stored fluid is transported to the heating portion to perform X-ray imaging (S331), and the temperature of the heating portion 123 is sensed (S332). In the case that the sensed temperature of the heating portion exceeds the predetermined temperature limit (S333), the amount of the fluid transported to the heating portion is reduced (S334). To this end, the degree of opening of the valve 162a provided at the outlet 151b of the heat storage portion 151 may be lowered, or the fan or pump provided to the heat storage portion 151 may be controlled to reduce the flow of the fluid toward the heating portion 123.

Sensing or measuring of the temperature of the heating portion may be performed in real time or at regular intervals. In the case that the sensed temperature of the heating portion is lower than a predetermined lower temperature limit (Yes in operation S335), the amount of the fluid transferred to the heating portion is increased (S336). To increase the amount of the fluid, the operations performed to reduce the amount of the fluid are performed in reverse.

If the amount of the fluid is insufficient (YES in operation S337), an auxiliary heat source is operated (S338) to supplement the heat supply. The auxiliary heat source is as described above in an exemplary embodiment of the X-ray imaging apparatus 100.

In the exemplary embodiment illustrated in FIGS. 16 to 18, the heat produced by the X-ray source 110 is stored and then used to heat the heating portion 123. However, exemplary embodiments are not limited thereto. As described above in an exemplary embodiment of the X-ray imaging apparatus 100, the heat storage portion 151 may be omitted and the heat produced by the X-ray source 110 may be immediately transferred to the heating portion 123 to heat the breast 30.

According to the X-ray imaging apparatus and control method for the same as described above, discomfort felt by the patient due to, for example, contact with a cold surface of the X-ray imaging apparatus 100 may be reduced by heating a portion of the X-ray imaging apparatus 100 contacting the breast. Particularly, since wasted heat which is dissipated during generation of X-rays is used, a separate heat source does not need to be provided. Therefore, the complexity of the apparatus and manufacturing costs may be reduced and energy may be saved.

As is apparent from the above description, by heating a portion of the X-ray imaging apparatus contacting the breast using the wasted heat, which is the heat produced during generation of X-rays, subject discomfort due to feeling cold may be reduced without using a separate heat source.

Although a few exemplary embodiments have been shown and described, it would be appreciated by those skilled in the art that changes may be made in these exemplary embodiments without departing from the principles and spirit of the inventive concept, the scope of which is defined in the claims and their equivalents.

What is claimed is:

1. An X-ray imaging apparatus which captures an X-ray image of an object, comprising:
   an X-ray source configured to generate and emit X-rays onto the object;
   an X-ray detector configured to detect the X-rays transmitted through the object and convert the detected X-rays into an electrical signal;
   a heating portion located at an upper portion of the X-ray detector and configured to contact a lower part of the object;
   a heat transfer portion configured to transfer heat produced in the X-ray source to the heating portion; and
   a thermal insulation member located between the X-ray detector and the heating portion configured to block heat from being transferred to the X-ray detector.

2. The X-ray imaging apparatus according to claim 1, wherein the heat transfer portion comprises a pipe through which a fluid heated by the heat produced in the X-ray source, flows.

3. The X-ray imaging apparatus according to claim 2, further comprising a flow regulator configured to regulate a flow of the fluid,
   wherein the flow regulator comprises at least one of a valve, a fan, and a pump.

4. The X-ray imaging apparatus according to claim 2, wherein the heating portion is heated by the fluid introduced into the heating portion through the heat transfer portion.

5. The X-ray imaging apparatus according to claim 4, wherein the heating portion comprises a passage through which the fluid circulates, and
   wherein the passage includes at least one curved portion.

6. The X-ray imaging apparatus according to claim 2, further comprising a heat storage portion configured to store the heat produced in the X-ray source, and
   wherein the heat storage portion is formed in the X-ray source or in the heat transfer portion.

7. The X-ray imaging apparatus according to claim 6, wherein the heat storage portion comprises a chamber configured to store the fluid heated by the heat produced in the X-ray source and a valve mounted to an outlet of the heat storage portion to control a discharge of the fluid stored in the chamber.

8. The X-ray imaging apparatus according to claim 3, further comprising a temperature sensor configured to measure a temperature of the heating portion and a temperature controller configured to control the flow regulator based on the temperature of the heating portion measured by the temperature sensor.

9. The X-ray imaging apparatus according to claim 8, wherein when the temperature of the heating portion exceeds a predetermined temperature limit, the temperature controller is configured to control the flow regulator to reduce an amount of the fluid introduced into the heating portion, or when the temperature of the heating portion is lower than a predetermined lower temperature limit, the temperature controller is configured to control the flow regulator to increase the amount of the fluid introduced into the heating portion.

10. The X-ray imaging apparatus according to claim 8, further comprising an auxiliary heat source configured to supply heat to the heating portion, and
wherein the temperature controller is configured to turn on the auxiliary heat source when the temperature of the heating portion is lower than a predetermined lower temperature limit.

11. The X-ray imaging apparatus according to claim 2, wherein the heating portion configured to contact the lower part of the object is a first heating portion,
and wherein the X-ray imaging apparatus further comprises:
a compression paddle configured to compress the object positioned on the first heating portion; and
a second heating portion mounted on a lower portion of the compression paddle configured to contact an upper part of the object.

12. The X-ray imaging apparatus according to claim 11, wherein the heat transfer portion is a first heat transfer portion, and
wherein the X-ray imaging apparatus further comprises a second heat transfer portion configured to transfer the heat produced in the X-ray source to the second heating portion.

13. The X-ray imaging apparatus according to claim 1, wherein the heat transfer portion comprises a wire through which the heat produced in the X-ray source is conductively transferred, and
wherein the heating portion includes a metal coil which is connected to the heat transfer portion.

14. The X-ray imaging apparatus according to claim 1, wherein an upper portion of the heating portion is made with a thermally conductive material, and a lower portion of the heating portion is made with a thermal insulation material.

15. The X-ray imaging apparatus according to claim 1, wherein the thermal insulation member comprises a film configured to block heat transfer.

16. The X-ray imaging apparatus according to claim 1, wherein the thermal insulation member comprises a coated layer coated with a material configured to block heat transfer.

17. The X-ray imaging apparatus according to claim 1, further comprising a display configured to display information indicating a status of the heating portion.

18. A control method for an X-ray imaging apparatus which captures an X-ray image of an object, the control method comprising
supplying electric power to an X-ray tube and producing X-rays and heat;
storing the produced heat in a heat storage portion; and
transferring the stored heat to a heating portion to contact an object.

19. The control method according to claim 18, wherein the storing comprises:
flowing a fluid around the X-ray tube and heating the fluid; and
transferring the heated fluid to the heating portion.

20. The control method according to claim 19, further comprising measuring a temperature of the heating portion and controlling an amount of the fluid transferred to the heating portion based on the measured temperature of the heating portion.

* * * * *